US011161236B2

(12) United States Patent
Mallinson

(10) Patent No.: US 11,161,236 B2
(45) Date of Patent: Nov. 2, 2021

(54) ROBOT AS PERSONAL TRAINER

(71) Applicant: Sony Interactive Entertainment Inc., Tokyo (JP)

(72) Inventor: Dominic Mallinson, Redwood City, CA (US)

(73) Assignee: Sony Interactive Entertainment Inc., Tokyo (JP)

(*) Notice: Subject to any disclaimer, the term of this patent is extended or adjusted under 35 U.S.C. 154(b) by 25 days.

(21) Appl. No.: 15/705,167

(22) Filed: Sep. 14, 2017

(65) Prior Publication Data

US 2019/0077007 A1   Mar. 14, 2019

(51) Int. Cl.
*A63B 24/00*   (2006.01)
*G05D 1/02*   (2020.01)
(Continued)

(52) U.S. Cl.
CPC ........... *B25J 9/0003* (2013.01); *A61B 5/1113* (2013.01); *A61B 5/1118* (2013.01); *A61B 5/1128* (2013.01); *A63B 24/0003* (2013.01); *A63B 24/0075* (2013.01); *A63B 71/0622* (2013.01); *G05D 1/0094* (2013.01); *G05D 1/0246* (2013.01); *G16H 20/30* (2018.01); *A63B 2024/0012* (2013.01); *A63B 2208/02* (2013.01)

(58) Field of Classification Search
CPC ... B25J 9/0003; G05D 1/0094; G05D 1/0246; G05D 1/0274; G16H 20/30; G06F 19/3481; A63B 24/00; A63B 24/0003; A63B 24/0006; A63B 24/0075; A63B 24/0081; A63B 2024/0009–0015; A63B 71/0622; A63B 2071/0636; A63B 2208/02–0295; A63B 2220/05; A63B 2220/806; A63B 2220/807; A63B 2220/83
See application file for complete search history.

(56) References Cited

U.S. PATENT DOCUMENTS

2004/0190754 A1   9/2004   Sakagami et al.
2012/0190505 A1   7/2012   Shavit et al.
(Continued)

FOREIGN PATENT DOCUMENTS

JP   2013-169611 A   9/2013
JP   2016-059658 A   4/2016

OTHER PUBLICATIONS

Boucher, Sol, "Obstacle Detection and Avoidance Using TurtleBot Platform and XBox Kinect", Aug. 9, 2012, Rochester Institute of Technology (Year: 2012).*

(Continued)

*Primary Examiner* — Spencer D Patton
(74) *Attorney, Agent, or Firm* — Penilla IP, APC

(57) ABSTRACT

Methods and systems for using a robot to provide feedback to a user when the user is engaged in a physical activity includes detecting presence of the user in a geo-location. The user is identified and associated with the robot. User activity in the geo-location is monitored and when the robot detects the user is performing an exercise from an exercise routine, the robot is positioned to one or more positions proximate to the user so as to capture image of a posture held by the user while performing the exercise. The captured image is analyzed and feedback provided to the user to allow the user to improve their posture.

25 Claims, 12 Drawing Sheets

(51) Int. Cl.
*B25J 9/00* (2006.01)
*A63B 71/06* (2006.01)
*A61B 5/11* (2006.01)
*G05D 1/00* (2006.01)
*G16H 20/30* (2018.01)

(56) References Cited

U.S. PATENT DOCUMENTS

2015/0202492 A1   7/2015   Domansky et al.
2017/0151500 A9   6/2017   Domansky et al.
2017/0244937 A1*  8/2017   Meier ................. H04N 5/23216
2017/0368413 A1* 12/2017   Shavit ................ A63B 24/0075

OTHER PUBLICATIONS

Estler, Daniel, "Path Planning and Optimization on SLAM-Based Maps", Oct. 31, 2016, University of Stuttgart, Bachelor Thesis Nr. 2493 (Year: 2016).*
Shara Kalana et al. _ "Mobile robotic active view planning for physiotherapy and physical exercise guidance", 2015 IEEE 7th International Conference on Cybernetics and Intelligent Systems (CIS) and IEEE Conference on Robotics, Automation and Mechatronics (RAM), Jul. 15, 2015, pp. 130-136, XP033206519, DOI: 10.1109/CCIS.2015.7274609, ISBN: 978-1-4673-7337-1.
ISR PCT/US2018/051241, Dated May 17, 2019, 5 pages.

* cited by examiner

OVERLAY OF CORRECT POSTURE 1
OVER CAPTURED POSTURE 1
(BODY PLANK)

OVERLAY OF CORRECT POSTURE 2
OVER CAPTURED POSTURE 2
(ELBOW PLANK)

CAPTURED POSTURE (FWD LUNGE)

CORRECT POSTURE (FWD LUNGE)

ROBOT AS PERSONAL TRAINER

FIELD

The present disclosure describes methods and system for engaging a robot as a personal trainer for a user by allowing the robot to monitor the postures of the user while performing an exercise routine and dynamically provide feedback.

BACKGROUND

Description of the Related Art

The advancement in computer technology has led to advancement in cloud based processing, video game technology, etc. With the advancement in cloud based processing, such as high powered graphics processors, users are presented with an interactive experience that is desirable and optimal. For example, cloud-based systems provide virtually unlimited processing power and system resources for execution of interactive applications, such as video games. The cloud-based systems make an overwhelming breadth of legacy and new interactive applications available for users to access and interact without having to upgrade their own devices. These cloud-based systems enable streaming of content to remote clients, wherein most processing is done on servers, which may be distributed. Cloud-based interactive applications, therefore, have been increasing in popularity because users find it easier to access more applications without complex hardware restrictions, and application developers find it easier to manage game code from centralized locations.

At a more personal level, personal devices are being developed to assist the users in selecting and interacting with content that is available on a remote server of a cloud-based system or on a local device, such as computer or console. For example, head mounted displays have been developed and are increasing in popularity as it allows the user to have an immersive interactive experience, such as immersive gaming experience, by allowing the user to interact with content presented on a display of the head mounted display. Similarly, various controllers have been developed to assist the user in providing inputs to the interactive content. The cloud-based system makes it easier to introduce newer devices as majority of the processing is done at the server level and newer devices can be easily integrated at the cloud level rather than at an individual system level.

In addition to controllers, robotic assistants are becoming more popular to assist the users in viewing and interacting with content. Early robotic assistants had limited capabilities and few options to facilitate user interactions.

It is in this context that embodiments of the disclosure arise.

SUMMARY OF THE INVENTION

Embodiments of the present invention disclose methods and systems that are used to assist a user to perform an activity, such as a physical training, with the help of a robot. Broadly speaking, a robot is associated with a user. The robot detects presence of the user in a geo-location where the robot is present. In response to detecting presence of the user, the robot monitors actions and interactions of the user in the geo-location. When the robot detects that the user is engaged in an exercise routine either based on the schedule followed by the user or based on explicit instructions received from the user, the robot moves into one or more positions proximal to the user so that the robot can capture images of a posture and motion of the user while the user is performing an exercise from the exercise routine. The robot uses the captured images to construct a model that mimics the posture of the user and queries a database to identify a virtual model that is defined for the particular exercise. The model is compared against the virtual model to identify differences in the model using, for example, machine learning techniques. The robot then provides feedback so as to assist the user in correcting the posture or movement for the different exercises defined in the exercise routine. The robot may continue monitoring the actions and motions of the user and provide additional feedback. The actions of the user may include a change in the posture of the user, which may be in response to the feedback or may be due to the user continuing with a different exercise in the exercise routine. The robot thus acts as a "Personal Trainer" providing feedback to the user, just like a real-life personal trainer, as the user is performing the exercise by capturing different angles of a posture and providing feedback on the posture.

In one implementation, a method is provided for assisting in physical training of a user using a robot. The method includes detecting presence of the user in a geo-location where the robot is deployed. The user is identified by matching user attributes of the user captured by the robot with corresponding user attributes stored in a user profile of the user. An exercise routine for performing in the geo-location is identified for the user. As the user begins performing the exercise routine, the robot is moved to one or more positions proximate to the user so as to capture a view of a posture held by the user when the user is performing an exercise from the exercise routine. The positions are identified based on the exercise that the user is currently performing. Feedback relating to the posture of the user is provided, based on the images of the posture captured by the robot, to allow the user to improve the posture, when performing the exercise.

In another implementation, a method for providing feedback for an exercise routine performed by a user, is disclosed. The method includes receiving instructions from the user, wherein the instructions identify the exercise routine that the user has selected to perform at a current time. Upon detecting the user performing the exercise routine, the robot is moved into one or more positions proximate to the user to capture a view of a posture held by the user when the user is performing an exercise from the exercise routine. The positions that the robot is moved to are identified based on the exercise performed by the user. Feedback related to the exercise routine is provided by the robot to the user to enable the user to improve the posture while the user is performing the exercise from the exercise routine. The robot is used to continue monitoring the posture of the user to determine any changes in the posture. When a change in the posture of the user is detected, the position of the robot or one or more sensors of the robot are adjusted to capture a view of the change in the posture of the user. Based on the detected change in the posture of the user, additional feedback is provided by the robot to the user to enable the user to improve the posture held by the user for the exercise.

In yet another implementation, a method for providing feedback using a robot, for an exercise routine performed by a user, is disclosed. The method includes receiving instructions from the user, wherein the instructions identify a specific portion of a body the user would like to target when exercising. The exercise routine that targets the specific portion of the body is identified, wherein the exercise routine includes different exercises that are to be performed by the user. Details of an exercise from the exercise routine are provided for the user to follow. Upon detecting the user performing the exercise, the robot is moved to one or more positions proximate to the user so as to enable the robot to capture an image of a posture held by the user while performing the exercise. The one or more positions to move the robot are identified based on the exercise that the user is performing. Feedback relating to the exercise is provided to enable the user to improve the posture for the exercise. As the user continues with the exercise routine, the posture of the user continues to be monitored, wherein the monitoring is performed by adjusting the position of the robot to capture changes in the posture of the user. Additional feedback is provided to the user based on the changes detected in the posture held by the user. The additional feedback is provided to enable the user to improve the posture for the exercise.

In another implementation, a system is disclosed. The system includes a robot communicating with a server hosted on a cloud system, over a network. The robot includes artificial intelligence (AI) logic that is configured to detect presence of a user in a geo-location in which the robot is present and to identify an activity that the user is scheduled to perform at a current time. The AI logic includes a plurality of logic modules that communicate with the server to obtain relevant information. The plurality of modules of the AI logic include a user identifier module, an exercise routine identifier module, a dynamic positioning module, a model builder module, a virtual model retriever module and a feedback generator module, to name a few. The user identifier module is configured to capture user attributes of a user present in the geo-location and to confirm identity of the user by matching the captured user attributes to a user profile of the user stored in a local memory of the robot or stored on the server. The exercise routine identifier module is configured to identify an exercise routine the user is scheduled to perform at a current time. The dynamic positioning module is configured to receive the exercise routine that the user is scheduled to perform and to identify one or more positions that are proximal to the user for moving the robot so as to be able to capture an image of a posture held by the user when the user performs an exercise form the exercise routine. The one or more positions to which the robot is to be moved are defined based on the exercise that the user is currently engaged to perform. The model builder module is configured to obtain the image of the posture held by the user to generate a model for the posture. The virtual model retriever module is configured to retrieve a virtual model defined for the exercise from an exercise routine database. The feedback generator module is configured to compare the model generated by the model builder module against the virtual model retrieved by the virtual model retriever module to identify any differences. Based on the differences identified in the model, the feedback generator module is configured to provide instructions to the user to correct or improve the posture for the exercise.

Other aspects and advantages of the invention will become apparent for one skilled in the art from the following detailed description, taken in conjunction with the accompanying drawings, illustrating by way of example the principles of the invention.

BRIEF DESCRIPTION OF THE DRAWINGS

The invention, together with further advantages thereof, may best be understood by reference to the following description taken in conjunction with the accompanying drawings.

DETAILED DESCRIPTION

Figure 1:
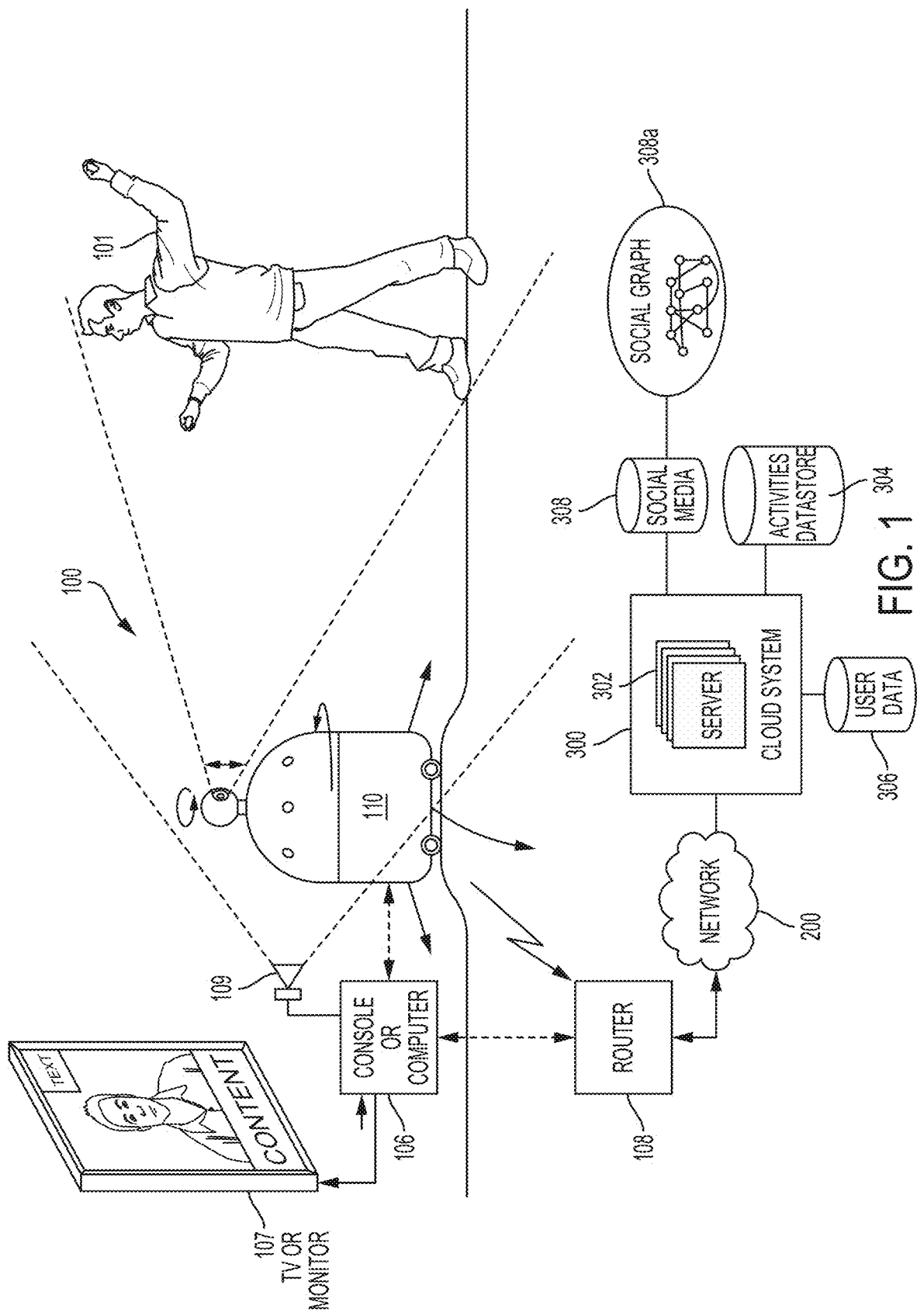
FIG. 1 illustrates a simplified block diagram of an example system that is used to detect presence of a user in a geo-location and to provide feedback to the user for activities performed by the user in the geo-location, in accordance with an implementation of the present invention.

In the following description, numerous specific details are set forth in order to provide a thorough understanding of the present invention. It will be apparent, however, to one skilled in the art that the present invention may be practiced without some or all of these specific details. In other instances, well known process steps have not been described in detail in order not to obscure the present invention.

According to various implementations of the present invention a robot is used to detect presence of a user in a geo-location, monitor an activity the user performs in the geo-location and provide feedback to the user. The feedback provided is to enable the user to improve performance of the activity and/or to encourage the user to perform the activity or additional activity. In some implementations, the activity may be related to an exercise routine and the robot is configured to monitor the user performing exercises from the exercise routine, capture images of the user performing the various exercises in the exercise routine and provide feedback to the user to improve performance of the exercise.

For example, the feedback may be provided for improving a posture for an exercise so that the user can reap the intended benefit out of the exercise routine. Alternately, the feedback may provide a status of the exercise routine or provide encouraging comments to the user to perform additional repetitions of an exercise or the exercise routine, or provide time-based comments, such as "hold the pose for 10 more seconds," etc., or provide comments to challenge the user to perform additional exercises from the exercise routine, or comments related to amount of calories burned, or comments based on historical performance, or to switch from one exercise to another. In some instances, depending on the type of exercise the user is performing and/or based on the activity history of the user, the feedback may also include suggestions of alternate exercise routines for the user. The alternate exercise routines may be identified based on the area or parts of the body the user is trying to target in his exercise routine. In some cases, the alternate exercise routines may be identified based on what is popular with other users (e.g., using crowdsourcing) having similar user attributes or interests. In some instances, the feedback may be provided in the form of an actual demonstration of the exercise or may be provided in an audio format, a video format, or an image format. The different formats may be delivered using appropriate components of the robot. For example, the audio format may be delivered through a speaker component, the video format may be projected using a projector component on to a display surface identified in the physical environment or may be transmitted (through wireless or wired communication links) to a head mounted display (HMD) worn by the user for rendering on a display screen of the HMD or may be rendered on to a display screen of the robot. In the case of a fully articulated humanoid robot, the robot may even demonstrate the correct posture.

After providing the feedback, the robot may continue monitoring the user to detect changes in the posture as the user continues his exercise routine. The changes in the posture may be due to the user adjusting the posture for the exercise based on the feedback received from the robot or may be due to the user performing another exercise in the exercise routine. The robot may move around to capture the changes in the posture of the user at different angles, analyze the changes and provide additional feedback to the user. The robot thus acts like a "Personal Trainer" to the user by observing the user performing each exercise, verifying the posture provided by the user for each exercise using virtual models, and providing feedback to enable the user to correct their posture when performing the exercise.

Although various implementations are discussed with reference to providing feedback to the user for performing an exercise routine, the implementations are not restricted to the exercise routine but can also be extended to provide feedback on any other observed activity of the user. With an overview of the invention, details of the various implementations will now be described with reference to the various drawings.

FIG. 1 illustrates a system in which a robot is used to track activity of a user 101 and to provide feedback to the user 101, in accordance with an implementation. A user 101 may be interested in performing an activity, such as an exercise routine, in a geo-location 100 and a robot 110 in the geo-location 100 that is associated with the user, is used to detect the user 101 performing the various exercises in the exercise routine, move into position proximal to the user to capture images of the user performing the exercise routine and provide feedback to enable the user to improve their posture when performing the exercises in the exercise routine. To assist in identifying the user 101 and providing feedback, the robot 110, in one implementation, may be communicatively connected to a computer 106 within a local area network using network interface. The communication connection may follow a wireless communication protocol. The computer 106 may be any general or special purpose computer known in the art, including but not limited to, a console, a personal computer, laptop, tablet computer, mobile device, cellular phone, tablet, thin client, set-top box, media streaming device, etc. The computer 106 may be used to match the user attributes of the user 101 in the geo-location with a corresponding user profile stored in the computer 106 and/or to identify scheduled activities of a user 101. In one implementation, the computer 106 may itself be a local network device, such as the router (although a separate router 108 is shown in FIG. 1), that does not perform any processing, but facilitates passage of network traffic.

Alternately, the robot 110 may itself be a networked device that connects to the network 200 directly to interact with a remote server 302 on a cloud system 300 via a router 108. The communication connection between the robot 110 and the router 108 may follow a wireless communication protocol although a wired communication protocol may also be contemplated. The remote server 302 may be used to identify the user 101 and/or to identify the scheduled activities of a user. In an alternate implementation, the robot 110 may interact with the remote server 302 through the computer 106 and the router 108. The communication connection between the router 108 and the network 200, in some implementation, follows a wired protocol although wireless protocol may also be contemplated.

The server 302 of the cloud system 300 may interact with user data datastore 306 to match user attributes of the user received from the robot 110 to a corresponding user profile. Once the user 101 is identified, the server 302 may query an activities datastore 304 to identify one or more exercise routines for the user. In one implementation, the exercise routine for the user may be identified based on the user's activity history. In alternate implementation, the exercise routine for the user may be identified based on what is popular with other users that share similar user attributes or goals. The exercise routine may be identified using crowdsourcing, for example, wherein the other users are social contacts identified from social graph(s) 308a associated with one or more social media 308 of the user. In an alternate example, the other users may be identified by matching the user's attributes with that of other users. This might be the case when there is no activity history for the user or when alternate exercise routines are being suggested for the user. Although it is shown that the data datastore 306 and activities datastore 304 as being part of the cloud system, a version of the data datastore 306 and activities datastore 304 may be part of the computer 106.

The user may activate the robot 110 by performing explicit actions, such as providing inputs using a controller (not shown) or through a head mounted display (HMD) (not shown) that the user may use when interacting with the computer 106 or worn by the user when performing the explicit action. In some implementation, the HMD may also be used to provide inputs to the robot 110 even when the user may not be wearing the HMD when performing an exercise routine. In such implementations, the HMD may act as another input device that can be used to provide inputs to the robot and to the computer 106. In one implementation, the controller and the HMD are communicatively connected to the robot 110, wherein the communication connection between the robot 110 and the controller, HMD follow a wireless or wired communication protocol. In an alternate implementation, the HMD and the controller may be communicatively connected to the robot 110 through the computer 106. In yet another implementation, the HMD, the controller and the robot 110 may all be networked devices that connect to the network 200 to communicate with the server 302 in the cloud system 300 and such connections to the network may be wired or wireless.

The inputs provided to the robot 110 from the HMD or the controller or any other input device are interpreted by the robot 110 to perform certain actions, such as detect the user in the geo-location and move into position to observe the user, when the user is performing certain activity, such as an exercise from an exercise routine. In alternate implementations, inputs provided by the user may include voice commands or inputs provided using a keyboard or mouse or other input device associated with the computer 106 that is communicatively connected to the robot 110, or through gesture or other inputs provided through a touch-screen of a monitor 107 associated with the computer 106 or the robot 110. In some implementations, the inputs provided through keyboard or other input devices may include the user identifier that is verified against user profiles stored locally in the robot 110 or in the computer 106 or remotely on the server 302 in a cloud system 300.

In alternate implementations, instead of receiving inputs (including user identifier) from the user, the robot 110 may detect the presence of a user in a geo-location where the robot 110 is deployed through one or more sensors, capture one or more user attributes using the one or more sensors of the robot 110 and verify the user using the captured user attributes. The sensors of the robot 110, for example, are configured to capture biometric data of the user and use the biometric data to identify the user. The user may be identified by matching the captured biometric data with user attributes of the user stored in a user profile. More details of the various sensors used to capture different biometric data will be discussed with reference to FIG. 3. In these alternate implementations, the robot automatically detects the presence of the user in the geo-location and verifies identity of the user without receiving explicit actions or input signals from the user. In one implementation, the user verification may be done locally using the user profile of the user stored in the robot 110 or on the computer 106. In an alternate implementation, the user verification may be done remotely by forwarding the user attributes captured for the user to the remote server 302 through the router 108 and the network 200 and allowing the server 302 to verify the identity of the user using the user profiles stored on the server.

In addition to capturing the user attributes of the user using the sensors in the robot 110, the robot 110 may also engage one or more image capturing devices (e.g., external camera) 109 to capture images of the user to further verify the user. In some implementations, the robot 110 may generate and forward a signal to activate the one or more external cameras 109 dispersed in the geo-location, upon detecting the presence of the user in the geo-location. The signal from the robot 110 may be transmitted directly to the external camera 109 (i.e., wireless communication) or may be transmitted through the computer 106 that is communicatively connected (i.e., wired or wireless communication) to the external camera 109. In response to the signal, the external camera 109 captures images of the user and transmits the captured images to the robot 110 using wireless communication protocol. The robot 110 may use the user attributes captured by the sensors and the images of the user captured by the one or more external cameras 109 to verify the user. In one implementation, the robot may have been previously associated with a particular user and the verification is to ensure that the user detected in the geo-location is the particular user that was previously associated with the robot. In another implementation, the robot may be associated with a new user whose presence was detected in the geo-location and the verification is to ensure that the new user is an authorized user to operate or interact with the robot 110. In such implementation, the association of the robot 110 to the new user may be temporal based and the association remains as long as the user is present in the geo-location.

Once the identity of the user is verified, the robot 110 may monitor the user to determine if the user is involved in any activity. Or alternately, the robot may identify and retrieve activities of the user scheduled for a current time. The robot may retrieve activities based on a command from the user or may automatically retrieve the activities, and such retrieval may be based on the user's schedule. In one implementation, the activities scheduled for the user may be retrieved from a local storage in the robot 110 or in the computer 106 or from a remote storage on the server 302. The activities scheduled for the user for the current time may be determined from an activity history for the user, based on a calendar entry, etc. Based on the scheduled activities retrieved for the user, the robot may identify an exercise routine the user is currently scheduled to perform and may determine the postures that the user is supposed to hold when performing the different exercises from the exercise routine. The postures for the different exercises may be identified from virtual models generated for the exercises. The robot 110 may then position itself in one or more areas in the geo-location proximate to the user so that the robot may be able to capture images of the user performing the exercises in the exercise routine. The images of the user performing the exercise may be compared against one or more virtual models and artificial intelligence (AI) logic within the robot 110 may be used to provide feedback to the user.

Figure 1A:
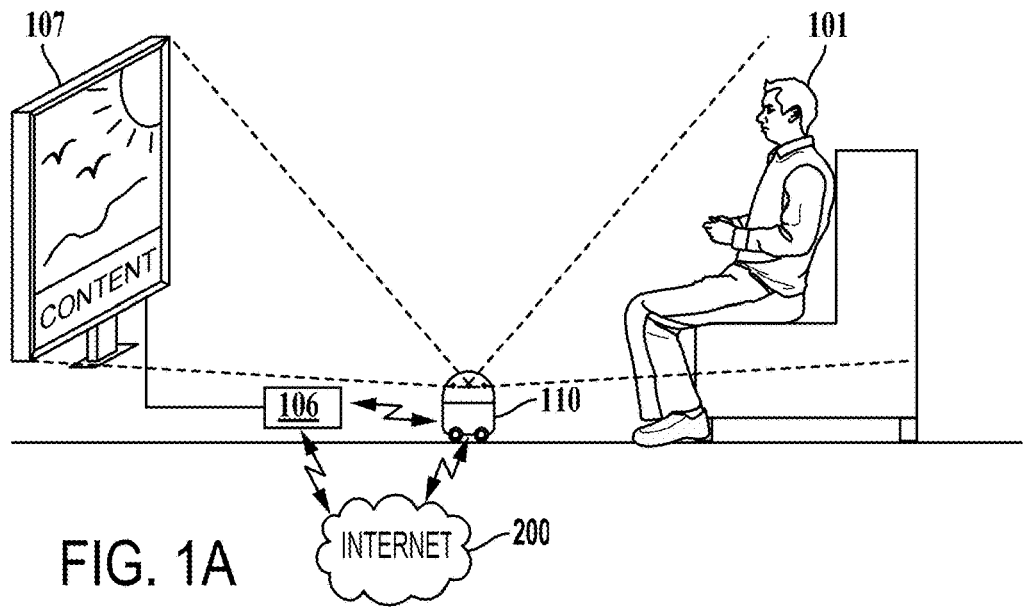
FIGS. 1A-1F illustrate various positions that the robot is moved to for capturing images of a user moving in a geo-location, in accordance to some implementations of the present invention.
Figure 1B:
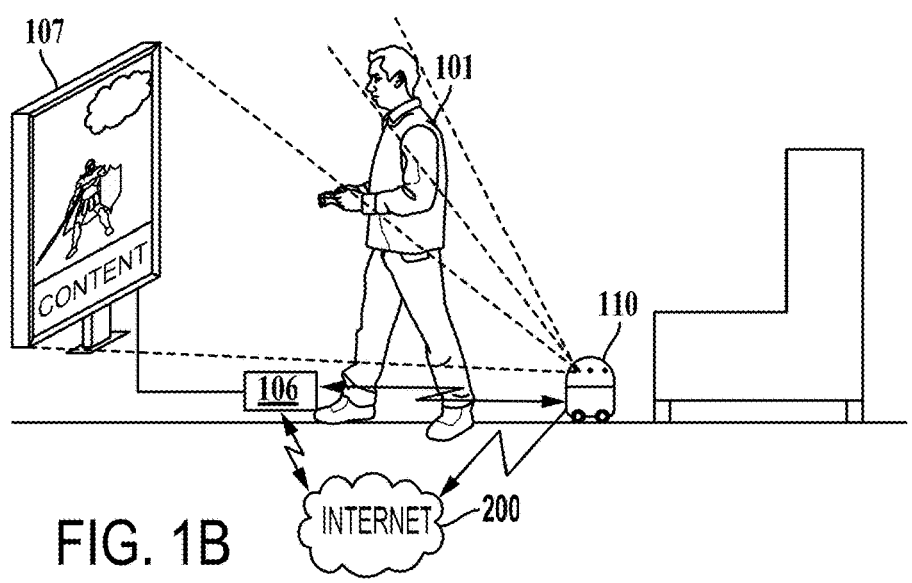
Figure 1C:
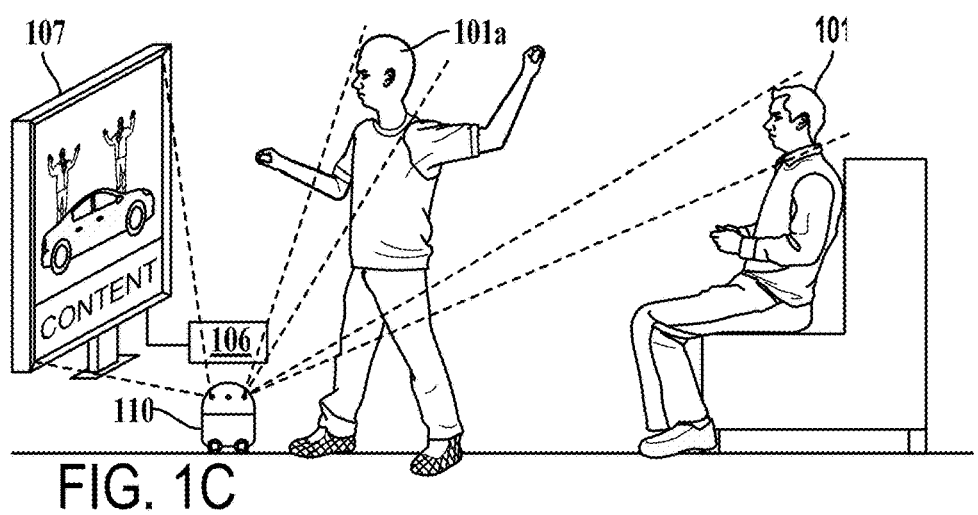

FIGS. 1A-1F identify the robot's role in monitoring the user's actions in a geo-location. In one embodiment, presence of the robot is detected in a geo location by tracking signals emitted by one or more signal emitting devices in the robot. The geo-location may be an indoor area, such as a house, an office building, a museum, etc., and the presence of the robot inside such geo-location may be determined using indoor geo-location tracking technique. For example, in some embodiments, the signals emitted by the signal emitting devices are Wi-Fi signals and the position of the robot in relation to a geo-location sensor can be determined based on the strength of the Wi-Fi signal. In some embodiments, when more than one geo-location sensor is available in the geo location, the position of the robot can be determined using triangulation technique, based on the emitted signals detected by the geo-location sensors. Once the robot is detected in the geo-location, the presence and actions of the user may be determined using the sensors in the robot. FIGS. 1A-1C illustrate some examples of the robot detecting presence of one or more users in the geo-location where the robot is present.

As shown in FIG. 1A, the user 101 is sitting on a chair and watching content presented on a monitor 107. The monitor may be a display portion of the computer 106 or may be a TV monitor that is connected to the computer 106. Cameras mounted on the robot 110 captures the images of the user 101 (as shown by broken pair of lines that are directed toward the user sitting on the chair) and of the monitor 107. These images may be processed locally at the computer 106 or sent remotely to the server 302 via the network 200.

FIG. 1B illustrates the robot 110 monitoring the movement of the user in a geo-location (e.g., a room) and capturing images of the user. As in FIG. 1A, images of the user 101 and images of the monitor 107 rendering content are captured by the robot. As shown, the robot has detected a change in the user's position (from a sitting position to a standing position) and location (from the chair closer to the monitor 107). The detection of the change in the user's position and location are recorded by the robot 110 using one or more capturing devices mounted on the robot 110. The robot 110 moves to an area that allows the robot 110 to capture the images of the user and of the monitor 107. It should be noted herein that it is not necessary that the robot capture the images of multiple objects of interest (e.g., user and the TV monitor, in this example) from a single location, as shown in FIG. 1B, but can be taken by moving to different locations.

FIG. 1C illustrates an alternate example wherein the robot 110 detects a second user 101a in the geo-location, monitors the actions of the user 101 and the second user 101a, and positions itself appropriately in the geo-location to capture the images of the user 101, the second user 101a and the monitor 107 and transmits the captured images to the computer 106 for processing. Although it is shown that the robot 110 captures the images of the user 101, the second user 101a and the monitor 107, from a single position, the robot 110 may be moved to different areas/positions in order to capture the images of all the objects, users that are of interest, from different angles or views. The captured images of the objects, users are analyzed to determine various attributes and aspects of the objects, users.

Figure 1D:
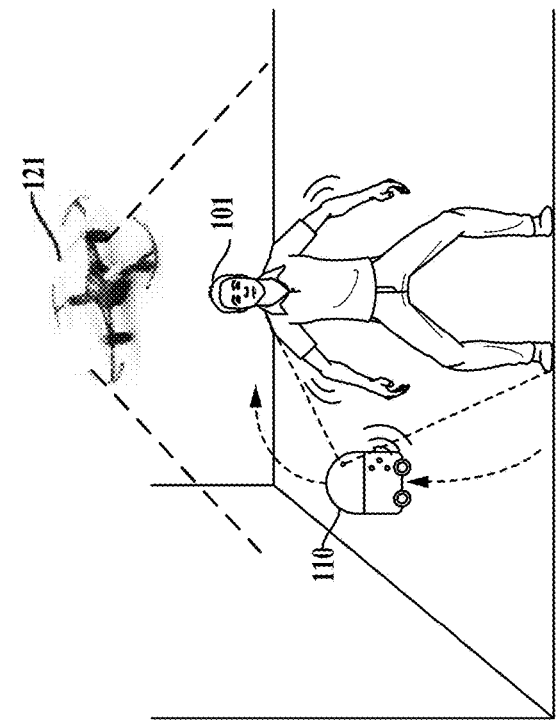
Figure 1E:
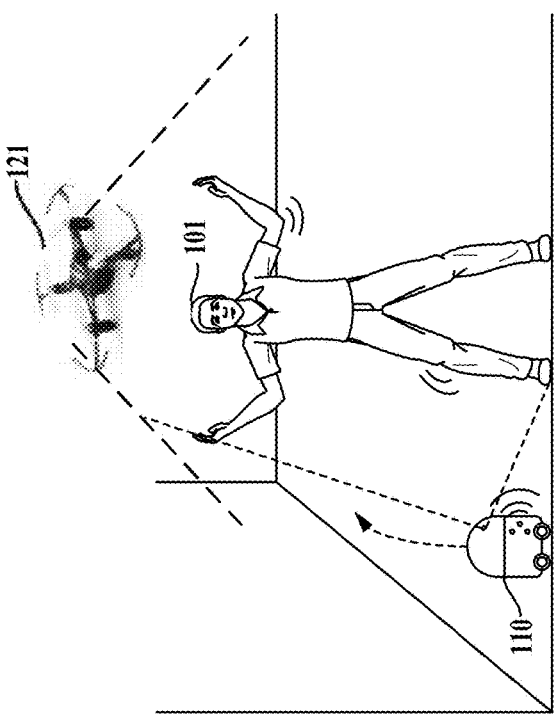
Figure 1F:
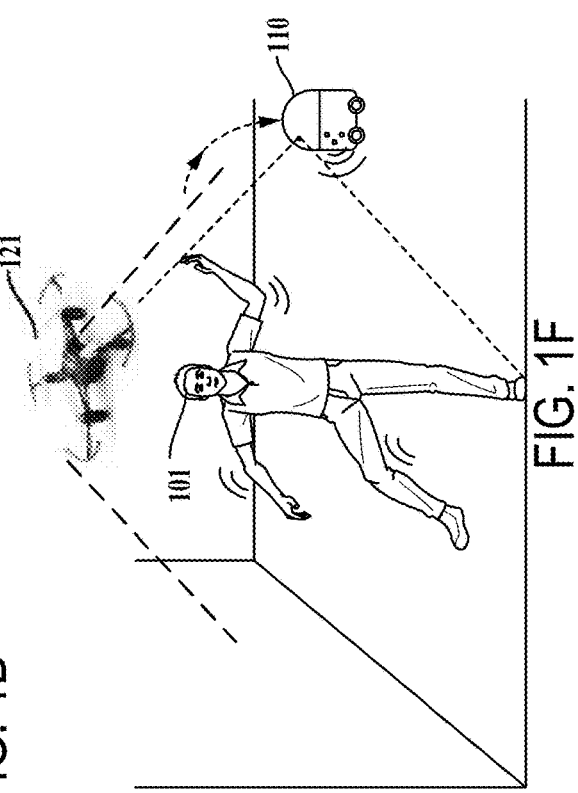

FIGS. 1D-1F illustrate one such implementation in which the robot 110 moves around to capture the image of the user 101. In addition to the robot moving to different positions, the robot 110 may deploy a drone 121, such as a quadcopter drone, over the area where the user is moving around in the geo location in order to capture the image of the user 101 from above. The drone 121 includes one or more sensors that are used in capturing the images of the user. As illustrated in FIG. 1D, the robot 110 is positioned in front of the user 101 and captures the image(s) of the user 101 as the user is performing an activity and the drone 121 is deployed to hover over the user in the geo location. As the user 101 continues to perform the activity, the robot 110 moves to the right side of the user to capture image(s) of the user 101 from a different perspective, as shown in FIG. 1E. The robot 110 captures the image of the user while the user is performing a semi-squat. The drone 121 may continue to hover over the user 101 in the same position or the position of the drone may be adjusted by the AI logic in the robot, upon detecting change in position or posture of the user while performing the activity, in order to continue to capture the image of the user as the user is performing the activity. For example, the position of the drone may be adjusted to hover over the top right side or top left side or top back side, or top front side or any other position so as to get a good view of the user as the user is performing the activity.

As the user continues to perform the activity, the robot 110 moves around to the left side of the user and captures the image of the user, as illustrated in FIG. 1F, while the drone continues to hover in the same position or an adjusted position. In some implementations, only the drone 121 is used to capture the images of the user. In such implementations, the position of the drone 121 is adjusted to capture the posture of the user. In alternate implementations, only the robot is used to capture the images of the user. In other implementations, both the robot and the drone are used in conjunction to capture the images of the user performing the activity, as illustrated in FIGS. 1D-1F. These images are forwarded to the computer 106 for processing. In some implementations, the robot itself may process the captured images and identify the exercise or activity the user is performing. In alternate implementations, the robot may forward the images to a computer communicatively coupled to the robot or to the network for onward transmission to the cloud system for processing by the server 302. Thus, the robot 110 detects the user moving in the geo-location and positions itself in appropriate locations in the geo-location to both monitor and capture the images of the user, which is then processed to provide feedback to the user.

FIGS. 2a-2g illustrate some example design implementations of the robot. The robot 110 includes a body that is mounted on wheels or treads or any other movable structure. The body includes a bottom structure 110a that is mounted on wheels or treads or other moveable structure and a top structure 110b that is disposed over the bottom structure 110a. The bottom structure 110a is used to house various parts of the robot that are used to perform various functions, such as sensing presence of a user, capturing user attributes of the user, retrieving user profile data, mapping the geo-location where the robot is deployed, moving the robot, performing sensor fusion of the data obtained from various sensors, processing various data, generating feedback, etc. Some of the parts of the robot that may be housed in the bottom structure 110a include a motor drive controller, a system board, a processor, a memory, storage, AI logic, etc. The bottom structure 110a may also be designed to provide charge stations for one or more controllers 104, one or more drones, etc. One or more universal serial bus (USB) ports, one or more image capturing devices, may also be provided in the bottom structure 110a. The outer side of the bottom structure 110a may include visual indicators to enable locating the robot in the geo-location.

A top structure 110b of the robot 110 may be designed to house various sensors, such as bio sensors, proximity sensors (e.g., ultrasonic sensors, motions sensors such as accelerometers, gyroscopes, magnetometers, radar, compass, etc.), one or more depth sensors (e.g., stereoscopic cameras, digital cameras, etc.), speakers, microphones, projectors, etc., that are used to capture various user attributes. In some implementation, the top structure 110b with the various sensors may be designed to rotate 360° along a horizontal axis, tilt at various angles, and also move along a vertical axis. In some implementations, the various sensors may be designed to extend outward from the body of the robot 110, during use, to enable the sensors to capture various aspects of an object that is under observation by the robot 110. In alternate implementations, the various sensors may be disposed in the bottom structure 110a, wherein the bottom structure is configured to rotate 360° along a horizontal axis. Further, in some implementations, the bottom structure 110a of the robot may be designed to move vertically and/or the sensors designed to extend outward from the body of the robot 110 so as to be able to capture different views of the object that is under observation. In some other implementations, the various sensors or additional sensors may be designed to be housed in a drone such as a quadcopter with a wireless link back to the robot or directly to the network.

Figure 2D:
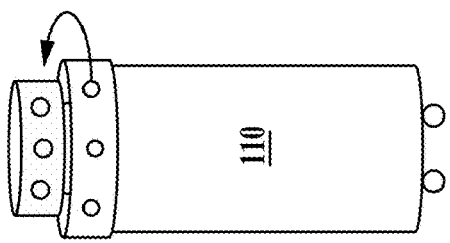
FIGS. 2A-2G illustrate various example design configurations of a robot that is used to capture image of a user and to provide feedback for the user based on an activity performed by the user, in accordance with several implementations of the present invention.
Figure 2C:
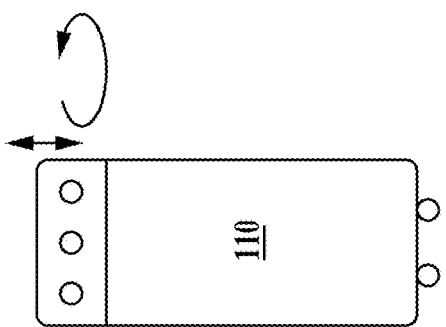
Figure 2B:
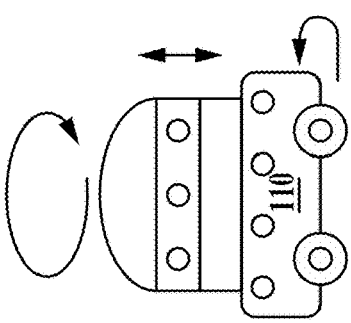
Figure 2A:
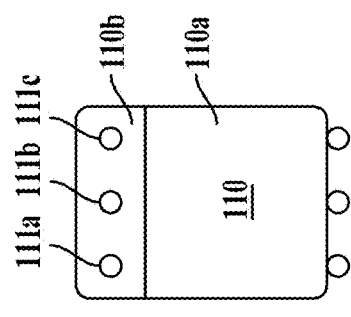

FIG. 2a illustrates one example design implementation of the robot 110 in which the bottom structure is provided on a carriage mounted on wheels. The wheel base could be of any format including wheels distributed uniformly along a perimeter of the carriage, a mecanum wheel, a tread, etc. The bottom structure 110a is also shown to be box-shaped. The top structure 110b is also shown to be box-shaped. The top structure 110b is also shown to be box-shaped. The top structure 110b is also shown to be box-shaped with one or more sensors 111a-111c distributed in a horizontal plane along an outer perimeter of the top structure 110b. The implementation is not restricted to distribution of the sensors along any single plane but could include other distribution configurations including a vertical plane, diagonally, inside bottom or top structure of the robot, etc.

FIG. 2b illustrates another example design implementation of the robot 110 in which the bottom structure 110a mounted on a wheel base is configured to spin along a horizontal axis. The bottom structure 110a is box shaped and includes some sensors mounted on the outer side. The top structure 110b is dome shaped on which a horizontal strip of sensors are mounted. In some implementations, the bottom structure 110a may be configured to rotate clockwise and the top structure may be configured to rotate anti clockwise. In another implementation, the top structure 110b may be configured to move along a vertical axis as well as spin radially to allow the sensors received therein to capture different views or detect different motions of the object under observation, while the bottom structure 110a may be configured to move radially along the horizontal axis.

FIG. 2c illustrates another example design implementation of the robot 110 in which the bottom structure is an elongated box that is mounted on a wheel base and the top structure 110b is designed to move radially along a horizontal axis as well as along a vertical axis. In this implementation, the sensors are shown to be disposed along an outer side of the top structure 110b. In alternate implementation, the sensors may be disposed along an outer side of the bottom structure 110a, as well. The implementations are not restricted to the sensors being on the outer side but can be disposed anywhere in the robot to capture a view or detect movement of the object of interest. The height of the bottom structure 110a may provide an advantage over the shorter robot in that the robot may be able to extend higher and be able to capture images or motion from a higher level. In some implementations, the sensors may be configured to extend outward to allow the sensors to capture images or motion of object of interest from different angles.

FIG. 2d illustrates another example design implementation of the robot 110, wherein the top structure 110b includes a circular lower portion and a rectangular upper portion. Both the circular lower portion and the rectangular upper portion include sensors distributed on the outer side or within to capture a view and/or a movement of an object of interest. As with the example design of FIG. 2b, the circular lower portion and the rectangular upper portion may be designed to rotate radially along a horizontal axis and/or move along a vertical axis. The rotation along the horizontal axis may be controlled to cause the upper portion to rotate at a different speed than the lower portion.

Figure 2G:
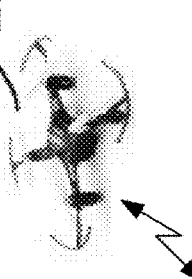
Figure 2G:
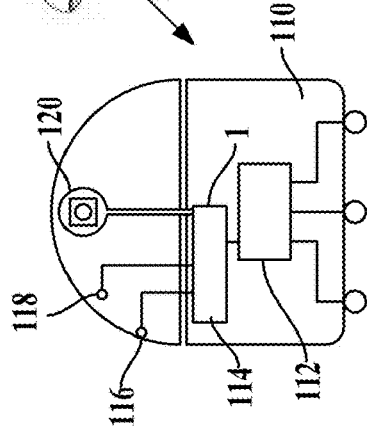
Figure 2G:
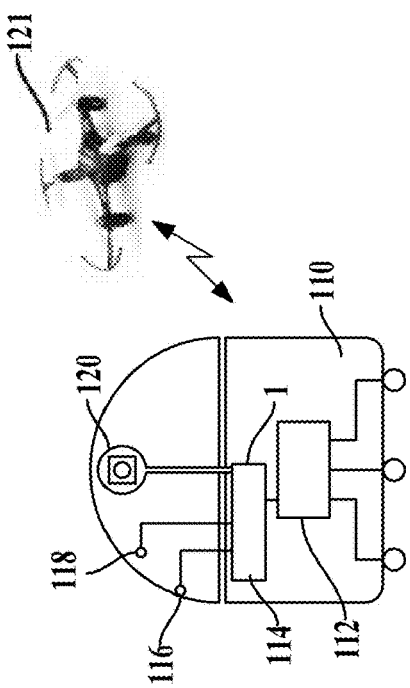
Figure 2F:
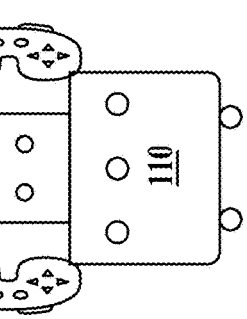
Figure 2E:
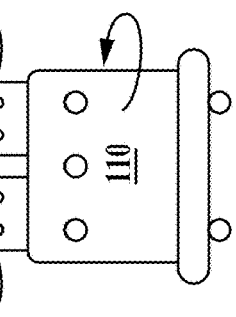

FIG. 2e illustrates another example design implementation of the robot 110 wherein the bottom structure 110a is disposed on a carriage that is mounted on wheels. The top structure is divided into two vertical portions. In one implementation, the bottom structure is configured to rotate along a horizontal axis. The two vertical portions of the top structure may each include a plurality of sensors disposed along an outer side or inside and may be individually or jointly controlled to move along a horizontal axis. In some implementation (not shown), the two vertical portions may also be configured to move along a vertical axis.

FIG. 2f illustrates another example design implementation of the robot 110. In this implementation, the bottom structure 110a is mounted on wheels and the top structure 110b is disposed over the bottom structure 110a. In the implementation illustrated in FIG. 2f, the robot houses two controllers, which are disposed in the form of arms. The controllers may be detached from the robot 110 and used by the user to provide inputs to either the computer 106 or to the robot 110. In such implementations, the robot 110 may be used to charge the controllers by providing a charging station in the bottom structure 110a. In some implementations, the controller may be a move controller that can be individually moved by the robot or any other type of controller that is configured to provide some input to the computer. In another implementation, instead of the controllers, one or more cameras or projectors may be provided at the bottom structure 110a. The cameras may be extended outward to capture images or movement of an object of interest from various angles and the disposition of the camera provides sufficient flexibility for capturing such images or movement. Similarly, a projector may be provided in the body of the robot. The projector may be used to project the images of the object captured by the various cameras disposed on the robot 110 or to project other images on display surface identified in a geo-location in the vicinity of the robot 110. The example implementations are not restricted to the controllers or cameras or projectors but can be extended to other sensors as well.

FIG. 2g illustrates an example implementation of a robot 110 showing some of the components used for performing various functions of the robot 110. The robot 110 includes a wheel base that is attached to wheels or treads. In some implementation, the wheel base may be a charging base that allows the robot 110 to get charged. The robot 110 includes a motor drive controller 112 in the bottom structure 110a. The motor drive controller 112 is connected to each of the wheels, for example, and is also communicatively coupled to a controller/system board 114. In the case where the robot 110 includes treads instead of wheels, the motor drive controller 112 is connected to the tread. In some implementation, the controller 114 is driven by artificial intelligence (AI) logic. Based on the AI logic, the controller 114 communicates with the motor drive controller 112 to move the robot around in the geo-location. Similarly, the controller 114 controls movement or function of the one or more cameras and/or other sensors of the robot 110 that are communicatively coupled to the controller 114. For example, signals generated by the controller 114 may control movement of the one or more cameras along a vertical and/or a horizontal axis to enable the cameras to capture movement of the user, images of the user and/or objects in the real-world environment in the geo-location. The controller 114 also includes communication interface that is used for communicating with the computer 106 or to the cloud system through the network via a router, in order to exchange data. One or more microphones 116 and one or more speakers 118 are provided in the robot to receive audio data or to provide audio comment. Sound captured by the microphone array may be processed to identify the location of a sound source. Sound from an identified location can be selectively utilized or processed to the exclusion of other sounds not from the identified location. The sensors, including audio and motion sensors within the robot, are used to detect sound and movement in the environment. The data is used to determine direction of the sound or movement, and triangulate to an area where the sound or movement is originating.

A processor in the robot 110 analyzes the images of objects in the geo-location captured by the one or more cameras and maps out the space in the geo-location, using techniques such as visual Simultaneous Localization and Mapping (vSLAM). The camera may include multiple image capturing devices (e.g., stereoscopic pair of cameras), an IR camera, a depth camera, or any combinations thereof. Based on the mapped space and based on the data obtained from the audio and motion sensors, the processor may triangulate to an area in the geo-location (where the robot 110 is deployed) from where the sound or movement is originating. The controller may then send out a signal to the drive controller to follow the sound or movement and move the robot 110 to the area or at least proximal to the area where the sound is originating and to capture images of the object, such as the user, that is making the sound. In some implementations, the space in the geo-location may be mapped to generate a two-dimensional map that identifies the boundary of movement (a geo fence) for the robot. The two-dimensional map is then used to direct the movement of the robot 110. Directing the robot 110 may include identifying a path of movement for the robot 110 around real-world objects identified in the geo-location. In other implementations, the space in the geo-location may be mapped to generate a three-dimensional map that identifies the volume of the geo location movement. In such implementations, the camera may be attached to a drone and the drone deployed from the robot 110, in response to the signal from the controller 114, to capture the volume of space in the geo-location. In alternate implementations, the volume of space may be captured by extending the one or more cameras upward so that the camera is sufficiently high enough to capture the volume of the geo-location. Using the two-dimensional or three-dimensional map of the space in the geo location, a path is identified for moving the robot or the drone. With the help of the proximity sensors, the robot 110 or the drone is manipulated to move proximate to the object (e.g., user) of interest. In some implementations, the robot may receive a signal from a HMD worn by the user, wherein the HMD is communicatively coupled to the robot 110. In such implementations, the signal generated by the HMD may be detected by one or more sensors (motion sensors, proximity sensors, etc.) of the robot 110, analyzed to identify the location of the HMD, and that of the user wearing the HMD, based on the mapped space and sensor data, and the robot is moved near the user wearing the HMD. In some implementations, in response to detecting the signal generated by the HMD, the robot may generate a signal to manipulate a drone 121 communicatively coupled to the robot 110, to a position proximate to the user in order to capture the image(s) of the user in the geo location.

Once the robot 110 and/or the drone 121 is in position proximal to the user, a signal from the controller 114 directs the one or more sensors of the robot 110 and/or the drone 121 to capture image or biometric data of the user, such as facial features, fingerprints, hand geometry, voice waves, DNA or signature, gesture, command, etc., and use the captured image or biometric data to identify the user. In some instances, the facial features that may be captured include retina and iris patterns, earlobe geometry, facial outline, gaze direction, etc. For instance, the captured biometric data or the image(s) are analyzed by the processor of the robot 110 to identify one or more user attributes, which are then used to identify the user based on the information cached in the memory of the robot 110 or may be sent to the computer 106 or to the cloud system for identifying the user.

Once the user is identified, the processor of the robot 110 may query an activity datastore or an activity scheduler (e.g., a calendar of activities, etc., that identifies the schedule of activities) to identify the activity the user is currently performing or is scheduled to perform. Based on the scheduled activity, the controller in association with the AI logic may send signals to appropriate sensors to capture the images of the user while the user is performing the activity and generate feedback for the activity.

Figure 3:
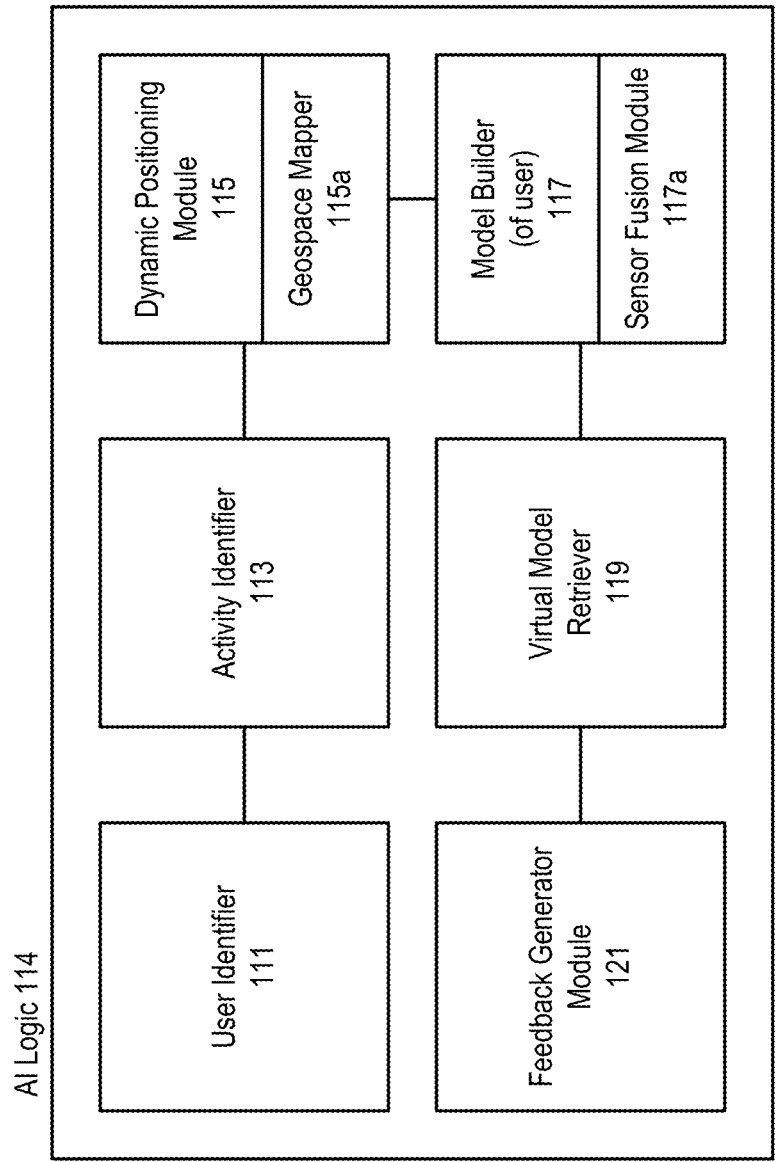
FIG. 3 illustrates example components of a robot used for monitoring user activity in a geo-location and providing feedback to the user, in accordance with an implementation of the present invention.

FIG. 3 illustrates some of the modules within the AI logic that are used in identify the user and providing feedback to the activity the user is performing, in one implementation. The AI logic is provided in the robot 110 to identify the user, determine the activity the user is engaged in performing, navigate the robot proximal to the user in order to observe the user performing the activity, generate appropriate feedback, etc. In some implementations, the AI logic in the robot 110 may communicate with additional AI logic that is on the cloud system to perform other functions. For example, the AI logic in the robot 110 may be used to learn the environment, map the space, identify different real-world objects in the space, determine areas that can be accessed by the robot 110, and adjust the position of the robot based on the mapped space.

The AI logic in the robot 110 may also capture the biometric data of the user and identify the user based on information that has been stored in its memory or send the data to the AI logic in the cloud to identify the user.

The AI logic 114 of the robot includes various modules to assist with the various functions of the robot. Some of the modules include a user identifier module 111, an activity identifier module 113, a dynamic positioning module 115, a model builder module 117, a virtual model retriever module 119 and a feedback generator module 121, to name a few. The above list of modules should not be considered exhaustive and that other modules may be included within the AI logic. The user identifier module 111 is used to identify a user in the geo-location where the robot 110 is present. The user identifier module 111 receives data captured through various sensors of the robot and/or input data provided through input devices and analyzes the data to identify the user. The data captured from the sensors may include biometric data, including facial features, voice, command, gesture, etc. Additionally, body attached sensors such as heart rate monitor or pulse oximeter can provide additional data for analysis and feedback. In such cases, the sensors in the robot are configured to receive signals from the body attached sensors the additional data provide signals to to transmit the additional data for analysis and feedback.

The input data may be provided by the user through one or more input devices, such as keyboard, mouse, controller, touch-screen, HMD, etc. As part of the analysis, the user identifier module 111 identifies user attributes which are then matched to a user profile that is stored in the local memory of the robot 110 or on the computer 106 or on the cloud system 300. In one implementation, the matched user profile is retrieved and a portion of the user profile is loaded to the robot. Loading of the user profile associates the robot to the user. In one implementation, the user profile associated with one robot is transferable to another robot connected to the same network (local area network, wide area network, cloud network, etc.). In an alternate implementation, the association of the robot may be switched from one user to another user. In such implementation, the robot is not associated with a single user but can be associated with any user that is detected in the geo-location and the loading of the user profile of a new user associates the robot to the new user. For example, if more than one user is detected in the geo-location, the robot can prioritize the users, match the user preferences of the prioritized user with a user profile and associate the user to the prioritized user by loading the user profile of the prioritized user onto the robot. In an alternate implementation, the matching of the user profile may be to verify that the user detected in the geo-location is the one that is associated with the robot. In some implementation, even when the robot is associated with a user, the robot may be able to load the user profile of another user. For example, when a second user is detected in the geo-location, the AI logic in the robot may compare the priority of the user associated with the robot and of the second user. If the second user has a higher priority, the robot may match the user attributes of the second user to a user profile and load the user profile of the second user so that the robot can now be associated with the second user. By loading the user profile of the user on to the robot, the AI logic 114 of the robot gets to know the user's personality, preferences, schedules, etc., and provide content in accordance to the user's preference. Additionally the user may select a personality for customizing the robot to reflect the user's preferences, such as the robot's voice and the style of instruction for a specific application, such as "boot camp" vs. "yoga" style for a physical fitness application, etc. Such user customization may be updated to the user profile and used during association of the robot to the user.

The activity identifier module 113, in some implementation, is configured to identify the activity of the user at a current time by querying an activities datastore available locally at the robot 110 or at the computer 106 or remotely at the cloud system 300, using the user identifier from the user profile. The activities datastore maintains a history of activities performed by each user over a period of time and the information gathered from the history is used to determine what activity the user is scheduled to perform at any given time. For example, the activity identifier module 113 may identify the exercise routines the user is scheduled to perform, and may also identify the number of repetitions that the user has to do or has previously done, which circuit training to follow for a particular day, personal bests and historical timings and durations, etc., and such information is extracted from the activity history. In an alternate implementation, the activity identifier module 113 may receive instructions or a command from the user indicating that the user is performing an activity and the instructions may identify the type of activity (e.g., sit-ups, pushups, pull-ups, jumping jacks, stretching, leg bends, squats, leg raises, jogging in place, treadmill, punching bag, etc.,) the user is planning to perform and number of repetitions the user intends to do at the current time. The activity identifier module 113 records the instructions and queries the activities datastore that is available locally at the robot or the computer 106 or remotely at the cloud system 300 to obtain the details of the exercises that are part of the exercise routine the user intends to perform. In another implementation, the user may just instruct the robot to identify the exercises that the user has to perform on a particular day and the activity identifier module 113 may access the activity history to know which exercise routine or circuit training the user is currently training on. In yet another implementation, the robot may be instructed to suggest an exercise routine for the user to target a particular body part and the activity identifier module 113 may access the social graph of the user or use crowdsourcing to identify the set of exercises that are popular with the social contacts of the user or with other users that share similar user attributes or fitness goal (i.e., targeting the identified body part).

The details of the exercises in the exercise routine are passed on to the dynamic positioning module 115. The dynamic positioning module 115 waits for the user to start an exercise from the exercise routine. When the robot detects that the user has begun his exercise (based on data captured by the various sensors, such as motion sensors, proximity sensors, etc., of the robot), the dynamic positioning module 115 will provide a signal to the controller to control the motor drive controller to move the robot 110 to one or more areas proximate to the user so that the sensors activated by a signal from the dynamic positioning module 115 may be able to capture images of the user performing the exercise. In order to identify the area proximate to the user, a geo space mapper module 115a of the dynamic positioning module 115 is used to map the space in the geo-location (in two-dimension format or three-dimension format) using the images captured by the various image capturing devices and the sensors. The mapped space is then used by the dynamic positioning module 115 to identify the area(s) where the user is in the geo-location, areas where real-world objects are (if any), area where the robot is currently positioned, areas around or proximate to the user that the robot can be moved to get a view of the user performing the exercise, and a path from the robot's current location to the area proximal to the user. The areas proximate to the user may be identified based on the type of exercise the user is performing and may change from one exercise to another. In some implementation, when the dynamic positioning module 115 cannot identify an area to move close to the user, the dynamic positioning module 115 may send out a request signal to the user requesting the user to move one or more real-world objects from the area proximal to the user, so that the robot can move into position or access the area near the user to capture images of the user performing the exercise. The request signal may be provided in audio format, video format or image format. The video format or the image format may be rendered on a rendering surface in the vicinity of the user or may be rendered on a display screen associated with a computer that is communicatively connected to the robot or on a display screen of the HMD, if the user is wearing the HMD or may be rendered on a display screen on the robot itself. The movement of the robot to the identified areas is assisted by the proximity sensors and other motion sensors of the robot so that the robot does not bump into any objects or people.

Figure 3A:
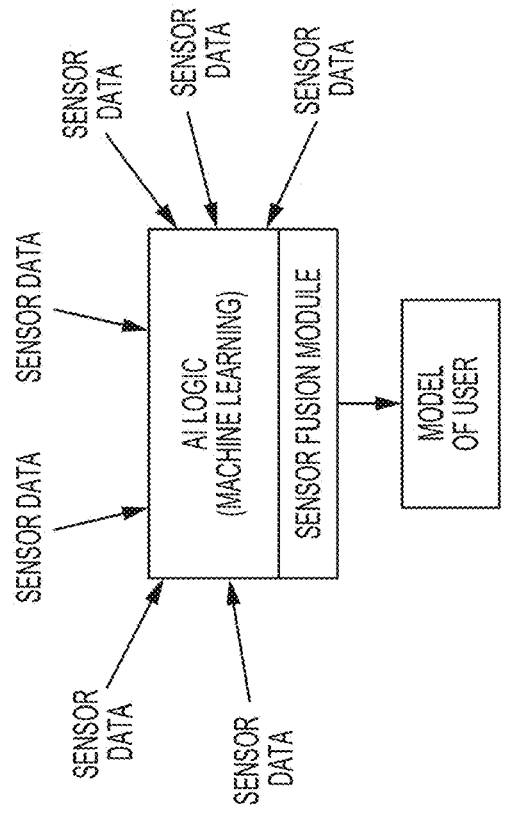
FIG. 3A illustrates an example implementation of a sensor fusion module within AI logic of the robot for generating a model of a user, in accordance to an implementation of the present invention.

Once the robot is moved into position(s), the model builder module 117 signals the controller to operate the various sensors in the robot to capture images of the user while the user is performing the exercise. In some implementations, the robot may be moved to multiple areas near the user to capture the images of postures held by the user, from various angles, while the user is performing the exercise. This is akin to a personal trainer moving around to monitor the posture(s) of the user. The images of the postures captured by the various sensors are used to build models of the user. In some implementations, the model builder module 117 may identify various angles of orientation of the user by tracking the position of the various limbs or parts of the user's body, motion, duration, angles, direction, velocity, acceleration, pivot points of the body, center of mass of the body, contractions of specific muscles, etc., and the various cameras and sensors of the robot can be positioned to capture such details in images and sensor data. In some implementation, the images and sensor data captured by the cameras and sensors may be used to determine when the user is feeling tired or uncomfortable (based on the redness in the face, racing of pulse, heartbeat, etc.) and to guide the user toward safety. The model builder module 117 engages a sensor fusion module 117a to which the data from the sensors and images from the camera are fed. FIG. 3A illustrates one such representation where the sensor fusion module 117a of the AI logic 114 receives data from various sensors (motion sensors, proximity sensors, cameras, image capturing devices, etc.,) as input, processes the data and outputs one or more models of the user. For example, the logic in the sensor fusion module 117a processes the data to generate models for a posture held by the user when performing an exercise. The models that are generated for a single posture may identify the posture from different angles or view points. In some implementation, the models are generated in substantial real-time. In some implementation, the models that are generated are stick-figure models that substantially mimic a skeletal outline of the posture held by the user. The stick-figure models include dots representing various pivot points and lines that represent the limbs or body parts on which the pivot points are located. In other implementations, the models that are generated are animated stick-figure models or three-dimensional models, representative models, etc.

Once the model of the user performing the activity (i.e., exercise) is generated, the virtual model retriever module 119 is engaged by the AI logic to identify virtual models for the exercise. The virtual models similar model representation as the generated models of the user, however, the virtual models identify the correct posture that needs to be held for each exercise. One or more virtual models may be identified for the exercise where each virtual model represents the correct posture for the exercise from a specific angle. The correct posture may also vary based on the user's progression from novice to expert or based on other factors such as age, weight and size.

The feedback generator module 121 then uses the identified virtual model(s) for the exercise and the model(s) generated from the captured image(s) of the posture of the user when the user was performing the exercise, to provide dynamic feedback as the user is performing the exercise. In one implementation, the feedback generator module 121 compares the generated model(s) of the user with the corresponding virtual model(s). Based on the comparison, the feedback generator module 121 generates the feedback identifying the differences in the two models. In some implementation, the generated feedback may include instructions to correct the posture based on the detected positional differences, or may provide encouraging tips to correct the user's posture when performing the exercise. For example, looking at the user's posture captured in the model, the AI logic in the feedback generator module 121 may instruct the user to push down more, stretch an arm or knee, straighten his leg or arm, etc. In addition to providing useful tips to correct the posture, the AI logic may also look at the user's activity history and provide status of repetitions performed previously while encouraging the user to perform additional repetitions. It may highlight progress, personal bests, durations of posture hold, etc. User comments or physical state are recorded by the AI logic and the feedback may be adjusted in accordance to the received comments or physical state. The dynamic feedback may also provide status of the same exercise routine followed by other users and provide instructions on how to improve the user's own performance. In some implementations, the AI logic may use information from crowdsourcing to determine the different exercise sequences followed by different users, determine the status of the exercise routine previously performed by the user obtained from the activity history, and tailor the exercise routine accordingly for the user.

The AI logic continues to monitor the user's activities by adjusting its position to obtain better perspective of the user while the user is engaged in the exercise routine. As the user proceeds to a next exercise in the exercise routine, the AI logic captures the changes in the posture, appropriately identifies the virtual models, compares the models generated for the user with the virtual models, and dynamically provides feedback to the user to improve the user's posture.

Figure 4:
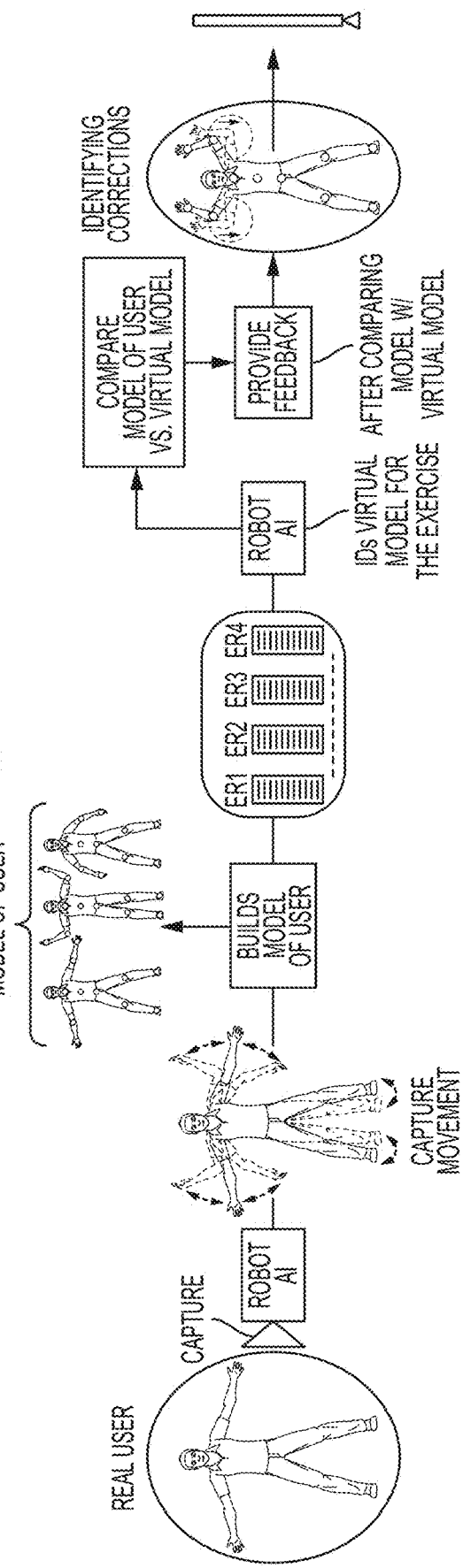
FIG. 4 illustrates flow of data for providing feedback to a user, in accordance to an implementation of the invention.

FIG. 4 illustrates simplified data flow diagram of an implementation. The data flow begins when the robot detects presence of a user in the geo-location. The presence of the user in the geo-location activates the AI logic, which then tracks the user's movement by activating various sensors and cameras of the robot. The activated sensors and cameras capture the image of the user while the user is performing an activity, such as an exercise (e.g., a jumping jack exercise). The AI logic then performs sensor fusion by merging the data received from the various sensors and builds one or more models of the user holding different postures while performing the exercise. The AI logic then queries database of virtual models to identify virtual models for the exercise routine. The AI logic then retrieves one or more virtual models for the exercise and compares the retrieved virtual models with the model(s) generated from the user's posture and generates feedback. The feedback may be in the form of an image that identifies areas where the posture needs to be corrected by the user. The image to correct any mistakes in the posture is provided for rendering on the TV monitor or via HMD. In some implementations, the mistakes may be highlighted in the image and necessary corrections provided either in textual format or audio format. Alternately, the feedback may be provided in an audio format or video format to encourage the user to perform additional exercises or additional repetitions of the same exercise, etc.

Figure 5A:
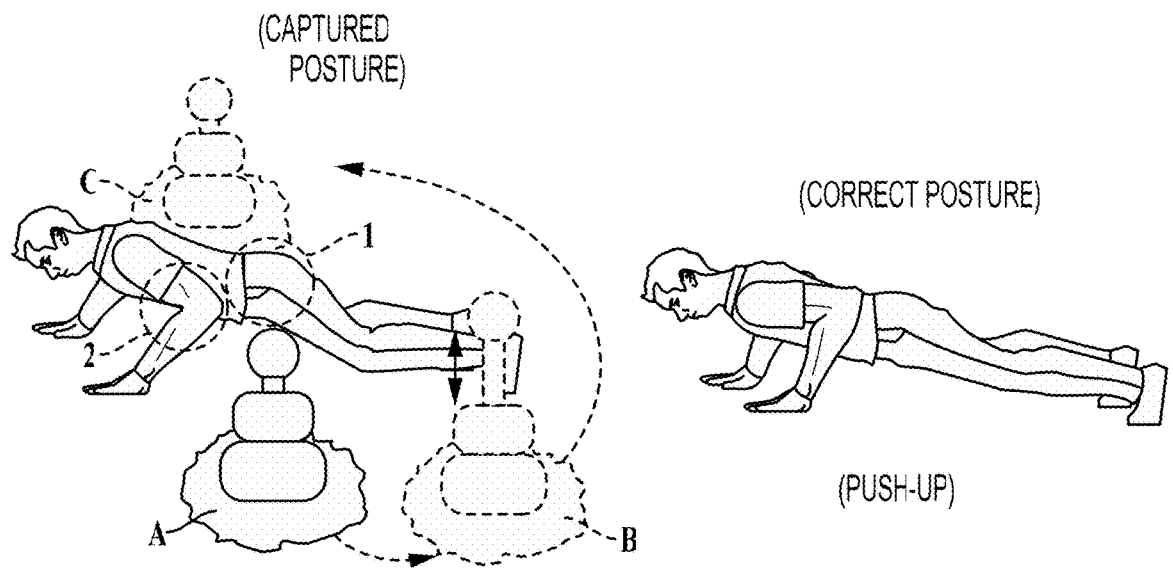
FIGS. 5A-5D illustrate examples of models generated by the AI logic of the robot for providing feedback to the user, in accordance to some implementations of the invention.

FIGS. 5A-5D illustrate some sample models generated for the user's various postures, the corresponding virtual models and the feedback that is provided to the user to improve his posture. FIG. 5A illustrates the various positions (areas A, B, C) from which the robot observes and captures images of the user performing a posture, such as a push-up. The images captured by the robot are compared to the virtual model and the differences 1 and 2 are identified. The AI logic then provides feedback either in an audio format or an image format. In some implementations, the AI logic may provide a video representation of the differences identifying the body part(s) of the user that needs to be corrected. In some implementation where the feedback is provided in image or video format, the virtual model identified for the exercise may be super-imposed over the model of the user and the necessary body parts that need to be adjusted are highlighted or otherwise identified. In some implementations, the image feedback may be accompanied with an audio feedback as well. In certain implementations where the robot is of humanoid form, the feedback could also include the robot demonstrating the correct posture.

Figure 5B:
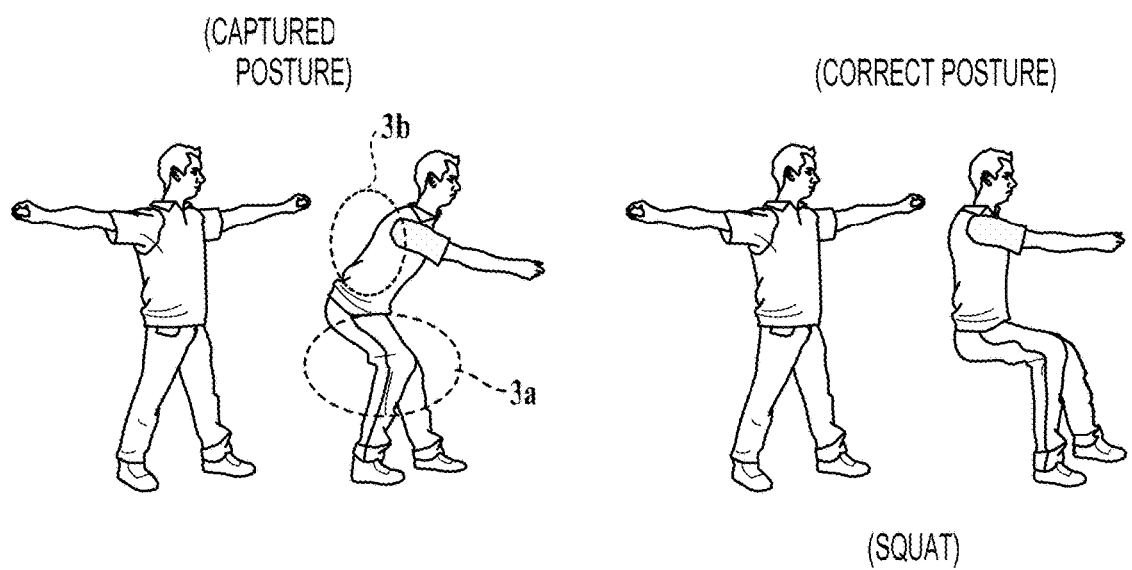
Figure 5C:
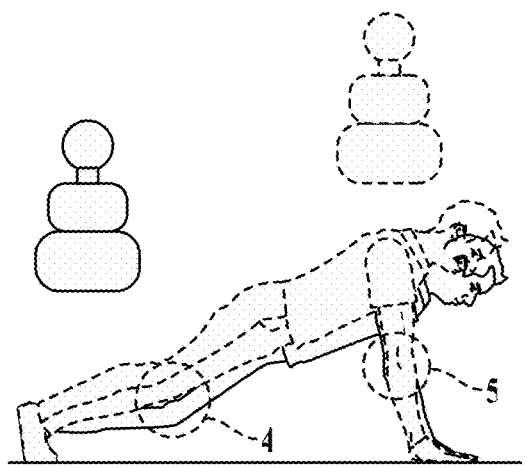
Figure 5C:
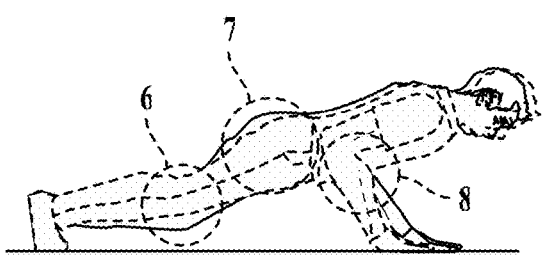
Figure 5D:
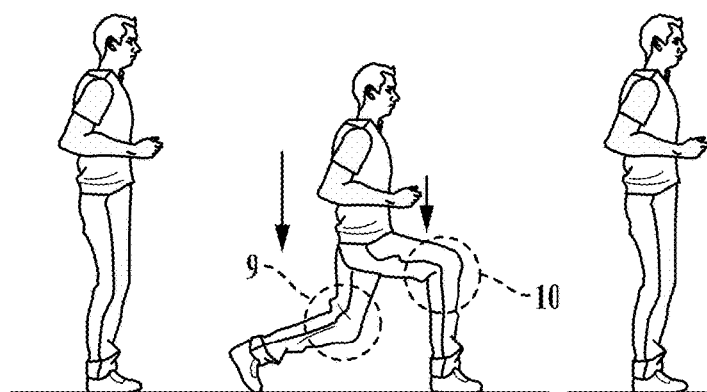
Figure 5D:

FIG. 5B illustrates an example model of a user generated when the user is performing another exercise in the exercise routine. In this example the user is performing squats. The AI logic may identify the difference (represented by broken circle 3) in the posture and appropriate feedback may be provided in audio, image or video format. FIG. 5C illustrates example models of a user performing body plank and progressing to elbow plank. As the user is performing the two exercises, the AI logic may dynamically position itself at various strategic positions to capture the postures of the user and use the captured postures to identify the differences (represented by broken circles 4, 5, 6 and 7) and provide feedback so that the user can correct the differences. FIG. 5D illustrates another example model of the user performing a set of exercises. In this implementation, the feedback may be provided in video format highlighting the differences between the user's postures and the postures obtained from the virtual models. The audio portion of the video may provide the corrective actions that need to be taken by the user for the set of exercises. In some implementations, the AI logic may identify a pre-defined instructional video or instructional audio for performing the exercise and present the instructional video or audio for the user to follow, as a feedback.

In some implementations, the AI logic in the robot is articulate enough to send signals to the controller to activate certain portions of the robot to demonstrate the correct technique. In other implementations, the AI logic may transmit the feedback to the HMD of the user so that the user performing the exercise is able to watch the correct postures of the exercise and perform it. In some implementations, the correct postures may be transmitted to the HMD of the user before the user wearing the HMD begins performing the exercise so that the user can follow the instructions and perform the exercise correctly. For example, after the robot determines the exercise routine the user is scheduled to perform and after detecting the user performing a first exercise in the exercise routine, subsequent exercises in the exercise routine may be projected to the user so that the user can follow the correct technique. In some implementations, the AI logic may provide music while the user is exercising. The music may be selected to match the fitness routine. The AI logic may also lower the volume of the music when feedback is being provided in audio format or when the user is providing instructions to the robot, and then raise the volume once the feedback or instructions have been provided.

Thus, the AI logic dynamically learns from the various interactions with the user and guides the user through the various fitness routines to improve the physical fitness goals set by the user. Additionally, the AI logic is able to customize the training sessions based on the user's historical and current performance, understand the user's online schedule by interacting with the user's online organizer, and use the online schedule to limit or extend the exercise routine based on the user's schedule, track the user's daily goal, provide encouraging messages to achieve the daily goal, and save the results in memory or on the server. Additionally, the AI logic may enable competition with other users using the respective robots as a friendly online competition amongst users, suggest other users or friends who have similar fitness goals to work out with, etc.

Figure 6A:
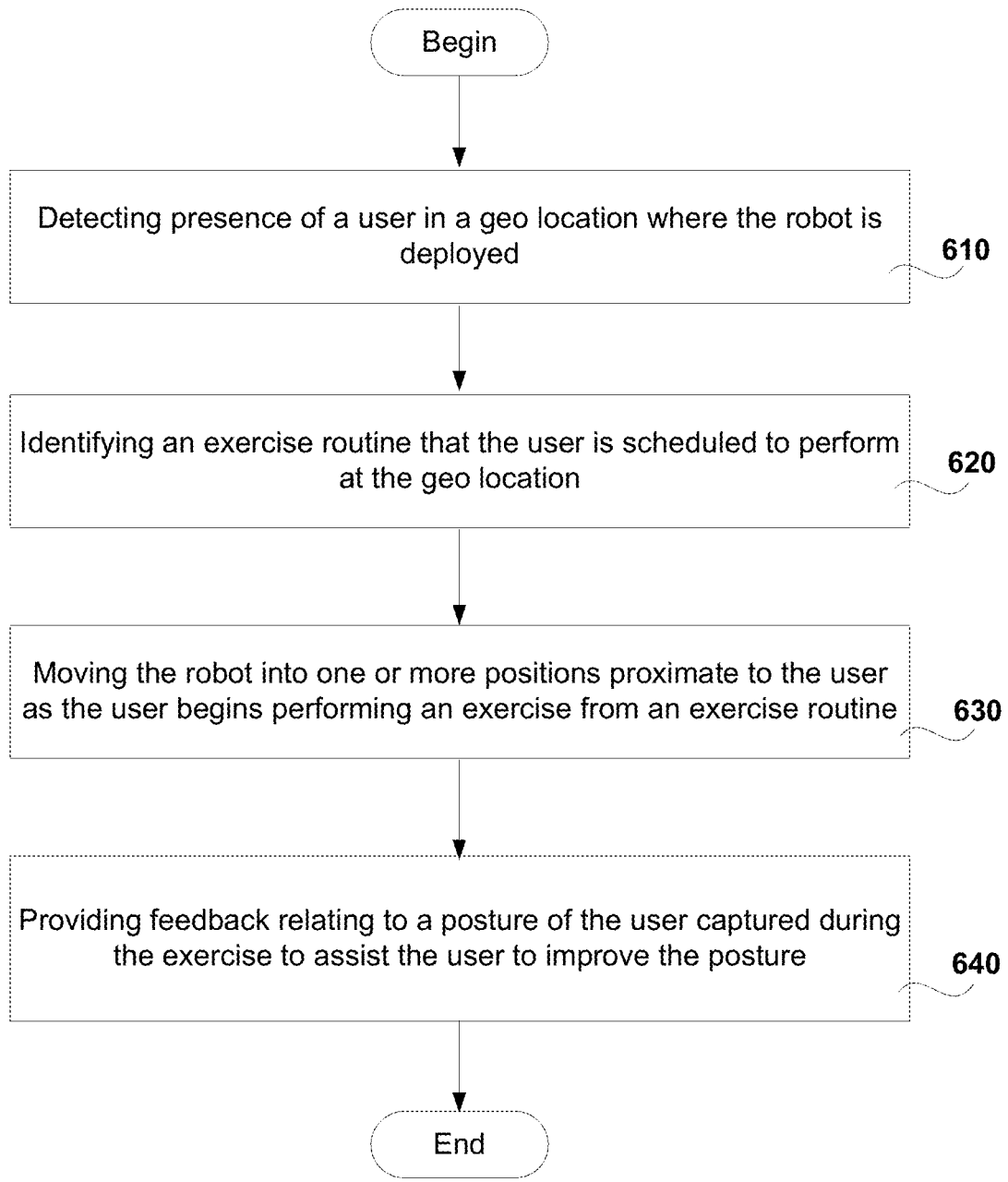
FIG. 6A illustrates process operations of a method that is used to monitor user activity in a geo-location and provide feedback to the user, in accordance with an implementation of the invention.

FIG. 6A illustrates operations of a method for using a robot to assist a user during physical training, in one implementation. The method begins at operation 610, when robot detects a presence of the user in a geo-location where the robot is deployed. The presence of the user in the geo-location may be detected based on a sound or movement from the user. The sound or movement of the user may be captured by one or more sensors in the robot. The user may provide verbal cues, such as instructions, detailing which physical training routine the user wishes to perform and such verbal cues are picked up by the microphone sensor in the robot. Alternately, movement of the user may be detected using motion sensors. In response to detecting the sound or movement, one or more sensors of the robot are engaged to capture biometric data, such as facial features, fingerprints, hand geometry, voice waves, DNA or signature, gesture, command, etc. The captured biometric data of the user is analyzed to identify user attributes, which are then used to identify a user profile of the user. The identified user profile is loaded to the robot so that the robot can be associated with the user. The association of the robot to the user allows an AI logic in the robot to get to know the user's personality, preferences, physical limitations, schedules, etc., and provide content in accordance to the user's preference.

Upon detecting the user in the geo-location, the AI logic determines the activity (e.g., exercise routine for physical training) the user is scheduled to perform, as illustrated in operation 620. As the AI logic already knows the user's schedule for different periods of time, based on the history of activity of the user, the AI logic may easily determine what activity the user will be engaged in, based on the activity history of the user.

When the user begins to perform an exercise from the exercise routine, the AI logic in the robot moves the robot into one or more positions proximate to the user, while the user is performing the exercise, as illustrated in operation 630. The various positions to which the robot can be moved may be identified by mapping the space in the geo-location using images captured by one or more image capturing devices of the robot. Based on the mapping and based on the type of exercise the user is currently performing, the AI logic may determine areas proximate to the user that can provide unobstructed view of the postures held by the user while performing the exercise. Using this information, the AI logic may identify a path of movement for the robot and instruct the controller to generate appropriate signal to the motor drive controller to cause the motor drive controller to move the robot to the identified area(s).

Once the robot is moved into position, the AI logic may instruct the controller to activate one or more sensors to capture the images of the user while the user is performing the exercise. The robot may determine the orientation of the user's limbs and body. Using this knowledge, the AI logic may provide instructions to position the robot near the user so that the sensors in the robot can capture such details of the user. Data from the various sensors may be fused together by the AI logic to generate model(s) of the posture(s) of the user. The generated model may be a skeletal representation of the user identifying pivot points, angles of orientation of the various limbs and parts of the body along the pivot points.

Using the generated model, the AI logic provides feedback relating to the posture captured for the exercise to assist the user to improve the posture for the exercise, as illustrated in operation 640. For example, as part of providing the feedback, the AI logic may identify and retrieve virtual models for the exercise performed by the user, compare the generated model against the virtual models, identify the differences (if any), and use machine learning algorithm to formulate the feedback and present the feedback to the user. The feedback may be provided in audio format, video format, or image format. In some implementations, the robot may be articulate enough to demonstrate the exercise technique or identify pre-recorded instructional audio or video and present the same to the user. The robot thus acts like a personal trainer by watching the user performing the exercise from different angles (i.e., by moving into different positions) and providing feedback to assist the user in correcting his posture, just like a live personal trainer would do. The robot may also record the instructions or audio cues provided by the user before or while performing the exercise, and adjust the feedback in accordance to the recorded instructions. While the user is performing the various exercises, the robot may also provide music while the user is performing the exercise. The music that is provided may correspond with the intensity of the exercise and as the intensity of the exercises change, the music may be adjusted to reflect the changes in the intensity.

Figure 6B:
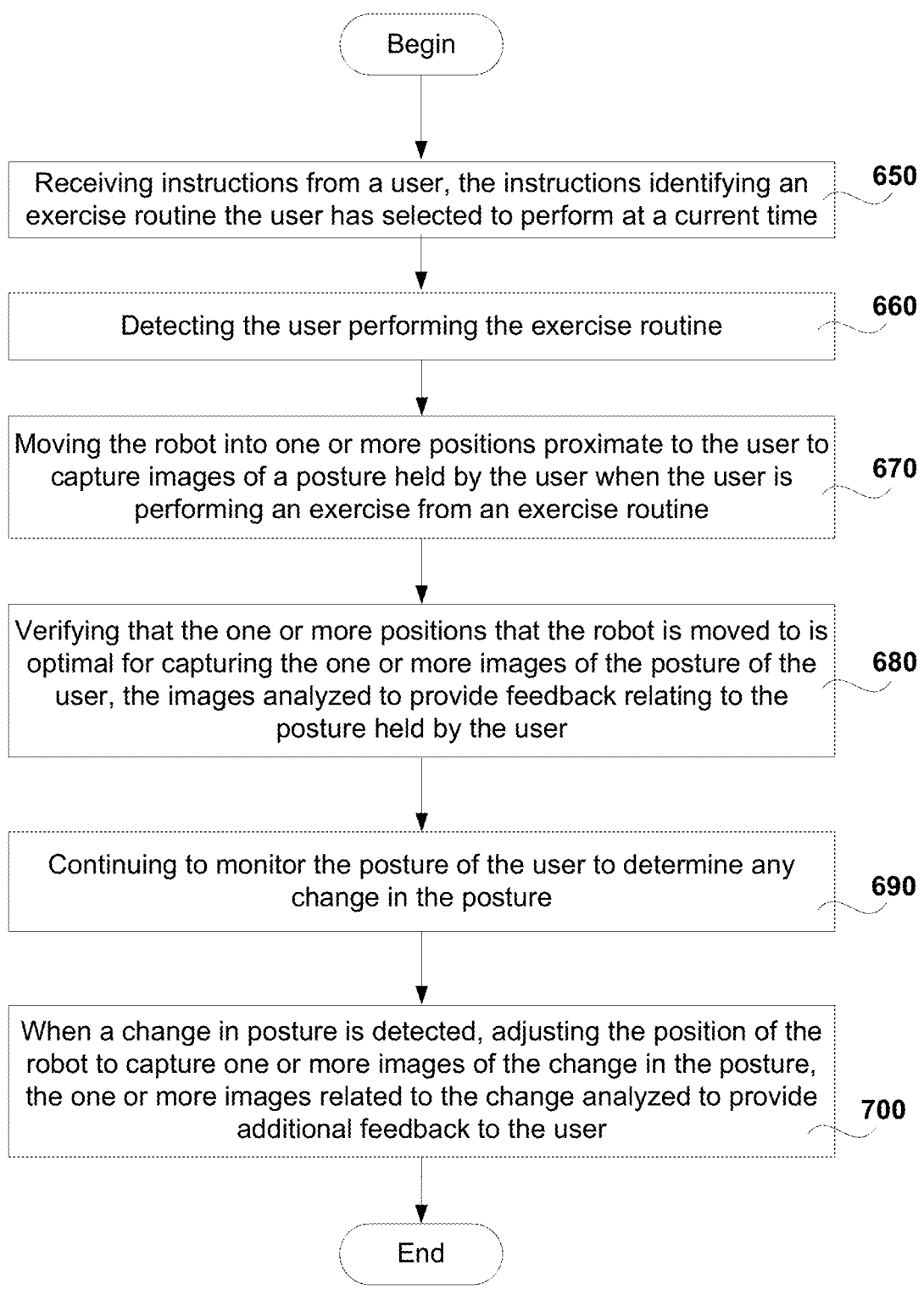
FIG. 6B illustrates process operations of a method that is used to receive instructions from a user, identify activity for the user to perform, and to provide feedback to the user, in accordance with an alternate implementation of the invention.

FIG. 6B illustrates operations of a method for using a robot to provide feedback for an exercise routine performed by a user, in an alternate implementation. The method begins at operation 650, when the robot receives instructions from the user. The instructions from the user may identify an exercise routine the user has selected to perform at a current time. The robot records the instructions and waits for the user to begin the exercise routine. One or more sensors of the robot are engaged to monitor activities of the user to determine when the user has begun the exercise routine. When the robot has detected the user performing the exercise routine, as illustrated in operation 660, the robot is moved into one or more positions proximate to the user to enable the robot to capture images of a posture held by the user, as illustrated in operation 670. Upon detecting the user performing an exercise from the exercise routine, AI logic in the robot may determine areas in the geo-location that are proximate to the user and send signal to the motor drive control to move the robot to those areas. The robot may engage motion sensors, proximity sensors, etc., to assist the robot to navigate to the area. Once the robot is positioned in an area identified by the AI logic, the sensors are directed to capture images of a posture held by the user while the user is performing an exercise from the exercise routine. The area the robot is moved to and activation of specific ones of the sensors to capture the posture of the user is driven by the exercise that the user is performing. For example, when the user is performing push-ups, the robot or at least one or more of its sensors may have to move to different areas (as shown in FIG. 5A) close to the user in order to capture the posture from different angles. When the user is performing jumping jacks or jogging, the robot may have to move to an area (e.g., area farther from the user) that allows the robot to capture the posture and movement of the various limbs at the same time.

The AI logic periodically verifies that the positions that the robot is moved to is optimal to capture the image(s) of the user performing the exercise, as illustrated in operation 680. As part of verifying, the AI logic may perform multiple tests by positioning the robot at different locations, capturing the images of the user, and analyzing the images to determine if the images properly capture the posture of the user. As part of the analysis, the captured images may be processed to determine if some of the image attributes, such as the lighting, resolution, angle of capture, orientation, distance from where the image of the user is captured, etc., are optimal. If not, position of the robot or one or more sensors are adjusted to affect the image attributes of the image(s) captured by the image capturing devices. Based on the analysis, the AI logic may determine which ones of the positions offer an optimal view of the posture(s) of the user while the user is performing the exercise. It should be noted that the positions identified for an exercise may keep changing, based on the exercise that the user is performing, and as a result, the verification may lead to dynamic re-positioning of the robot. For example, if the user elects to jog as part of his exercise routine, the robot may have to follow the user or move to different positions along the path followed by the user to capture the images. The images captured for the user performing the exercise are analyzed and feedback is provided to the user. Performing the analysis includes building a model representation of the user and comparing the model representation against virtual models that are available for the exercise to identify any differences. The AI logic may use its machine learning algorithm to formulate an appropriate feedback to the user and such feedback may be provided to correlate with any difference identified by the comparison. For example, the feedback may include instructions to adjust the orientation of different parts of the body (e.g., straighten your arm, stretch your leg, lift your back, fold your arm at 90°, etc.) when performing the exercise. When no differences are identified by the comparison of the two models, the feedback may be provided to encourage the user to perform additional exercises, or additional repetitions of the exercise, etc. In some implementations, the AI logic may also keep track of the type and number of exercises the user has performed and provide the status of the exercise routine to the user with encouraging comments to motivate the user to complete the exercise routine. In some implementations, the feedback may be provided using sign language, or may be provided in any language that is native to the user. In some implementations the AI logic may provide the user with optional robot personalities. For example, the option may include a strict "boot camp" style personality vs. a relaxed "yoga" style personality. Additional options may include an option to use male voice vs. female voice.

After providing feedback, the robot continues to monitor the user to determine if any change in the posture is detected, as illustrated in operation 690. The change in posture may be a result of the user following instructions provided in the feedback to correct the posture or may be a result of the user continuing with other exercises in the exercise routine. When a change in the posture is detected, as illustrated in operation 700, the AI logic senses the change and sends a signal to dynamically adjust the position of the robot to capture the image of the change in the posture, as illustrated in operation 710. This may include moving the robot to different areas or to continue capturing the image of the posture from the current position of the robot. The AI logic analyzes the captured changes in the posture and provides additional feedback, as illustrated in operation 720. As part of the analysis, the AI logic dynamically builds the model representing the change, determines if the change in the posture is for the same exercise or for a different exercise, and compares the newly built model of the user with appropriate virtual models to provide the feedback. The feedback is provided to allow the user to improve their postures to gain maximum benefit out of the exercise routine.

In another implementation, the robot may be used in a "tele-presence mode". In this implementation, the robot is used to capture images of a user performing an exercise from an exercise routine. The captured images are then forwarded to a remotely located user, such as a remote professional trainer. The remotely located professional trainer is able to view the captured images and provide feedback to the user from the remote location. The feedback may be provided synchronously or asynchronously. In this implementation, the AI logic is used to position the robot or a drone communicatively coupled to the robot, proximate to the user so as to capture the image(s) of the user performing an exercise and to communicate the feedback received from the remotely located user to the user performing the exercise.

In one implantation, a method for providing feedback for an exercise routine performed by a user, using a robot, is described. The method includes detecting a user performing the exercise routine. The user performing the exercise routine may be detected using one or more sensors of the robot. In response to detecting the user performing an exercise from the exercise routine, the robot is moved into one or more positions proximate to the user to enable capturing of one or more images of a posture held by the user, when the user is performing the exercise. The one or more positions to move the robot may be identified based on the exercise that is being performed. In some implementations, the robot may also employ a drone to capture the images of the user while the user is performing the exercise. The images captured by the robot and/or the drone are then forwarded to a remote user for comment. The remote user may view the images and provide comments, in the form of feedback. The feedback may be presented in an audio format, an image format, a video format, or any combination thereof. The robot receives the feedback and presents the feedback to the user. The feedback to the user is to assist the user to improve the posture while performing the exercise. In some implementations that employ a humanoid robot, the remote user may generate a signal with instructions to the robot to demonstrate the proper way of performing the exercise routine. The instructions in the signal may identify various body parts that need to be moved and the robot may interpret the feedback and demonstrate the correct posture for the exercise. For example, the signal may be an audio signal that instructs the humanoid robot to move certain body parts in a specific manner and the AI logic in the humanoid robot would interpret the instructions and demonstrate the moves for the exercise. In some implementations, the robot may perform the exercise in accordance to the instructions received from the remote user, and while performing the exercise may also capture images of the user performing the exercise and forward it to the remote user for further feedback. As can be seen, the AI logic of the robot may be used to detect presence of the user, capture images of the user performing an action, provide instantaneous feedback on the action or adopt a tele-presence mode and forward the images to a remote user for comment, which is used to provide feedback to the user performing the action.

The various implementations discussed herein provide a way to use a robot as a personal trainer to assist the user in his physical training. The AI logic in the robot identifies the various activities the user is involved in over a period of time, learns the user's preferences, likes, behavioral attributes, etc., through periodic interactions with the user and uses such learning to tailor the feedback to the user. For example, a novice user who starts out on a rigorous exercise routine may be provided with a more lenient feedback while a conditioned user may be provided with more precise and critical feedback. Further, as the novice user matures into a conditioned user, the feedback provided by the robot also transitions from lenient to critical to match the capabilities of the user to the exercise routine. In some implementations, as part of providing feedback, the robot may itself demonstrate the correct technique. The various implementations are not restricted to the realm of personal training but can be extended to other interactive applications, as well. For example, the robot may be used for providing feedback to the user when playing online games or when interacting with other online applications. As the user first begins playing the online game the AI logic may provide useful game playing tips to allow the user to progress in the game. In this example, the user may be playing the game by instantiating the game on a game console or computer or by interacting with a cloud system, and game play of the game may be projected on to a screen of the HMD or on a display surface in the vicinity of the user in the geo-location where the robot is present. The AI logic of the robot receives information on the game state of the game that the user is engaged in from the game console or computer or the cloud system. The AI logic also receives game logic that provides the details of the game including how the game progresses at different stages of game play. Using this information and based on the game state of the game, the AI logic may provide tips as feedback to the user to allow the user to progress in the game. The tips provided to the user are tailored to the user based on the user's skill level. As the user's game playing skills improve, the feedback is adjusted to match the user's improved skill level. Thus, the AI logic of the robot can be used to train the user or to provide useful tips to the user for interacting with any interactive online application and is therefore not restricted to physical training or online game. Other advantages of the various implementations may be envisioned by one skilled in the art.

Figure 7:
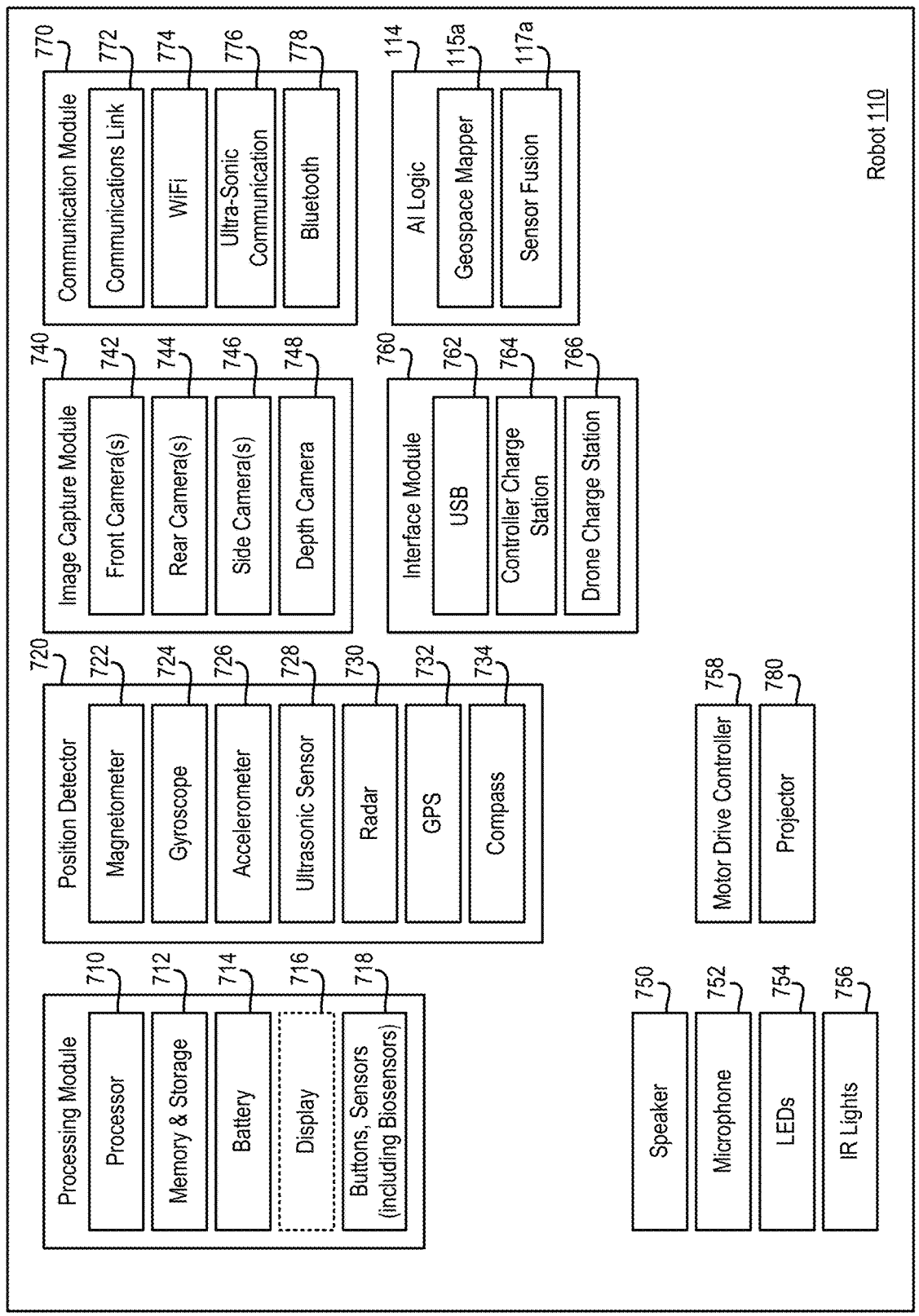
FIG. 7 illustrates various components of a robot that is used for monitoring activities of a user and providing feedback, in accordance with an implementation of the invention.

With reference to FIG. 7, a diagram illustrating components of a robot 110 is shown, in accordance with one implementation. The robot includes a processor 710 for executing program instructions. A memory 712 is provided for storage purposes, and may include both volatile and non-volatile memory. An optional display 716 is included which provides a visual interface that a user may view. A battery 714 is provided as a power source for the robot 110. In addition to the battery, the robot 110 may be mounted on a wheel-base which may also act as a charger to charge the robot. A position detector module 720 may include any of various kinds of motion sensitive hardware, such as a magnetometer 722, a gyroscope 724, an accelerometer 726, an ultrasonic sensor 728, a radar 730, a GPS 732 and a compass 734.

An accelerometer 726 is a device for measuring acceleration and gravity induced reaction forces. Single and multiple axis models are available to detect magnitude and direction of the acceleration in different directions. The accelerometer is used to sense inclination, vibration, and shock. In one embodiment, multiple accelerometers 726 (e.g., 3 accelerometers) are used to provide the direction of gravity, which gives an absolute reference for two angles (world-space pitch and world-space roll).

A magnetometer 722 measures the strength and direction of the magnetic field in the vicinity of the robot. In one embodiment, three magnetometers 722 are used within the robot, ensuring an absolute reference for the world-space yaw angle. In one embodiment, the magnetometer 722 is designed to span the earth magnetic field, which is ±80 microtesla. Magnetometers 722 are affected by metal, and provide a yaw measurement that is monotonic with actual yaw. The magnetic field may be warped due to metal in the environment, which causes a warp in the yaw measurement. If necessary, this warp can be calibrated using information from other sensors such as the gyroscope 724 or the camera. In one embodiment, accelerometer 726 is used together with magnetometer 722 to obtain the inclination and azimuth of the robot 110.

A gyroscope 724 is a device for measuring or maintaining orientation, based on the principles of angular momentum. In one embodiment, three gyroscopes 724 provide information about movement across the respective axis (x, y and z) based on inertial sensing. The gyroscopes 724 help in detecting fast rotations. However, the gyroscopes can drift overtime without the existence of an absolute reference. This requires resetting the gyroscopes periodically, which can be done using other available information, such as positional/ orientation determination based on visual tracking of an object, accelerometer, magnetometer, etc.

An ultrasonic sensor 728 is a device that can measure the distance of an object by using sound waves. It measures distance by sending out a sound wave at a specific frequency and listening for that sound wave to bounce back. By recording the elapsed time between the sound wave being generated and the sound wave bouncing back, it is possible to calculate the distance between the ultrasonic sensor and the object.

A radar 730 is an object-detection system that uses radio waves to determine the range, angle, or velocity of objects. A radar system consists of a transmitter for generating electromagnetic waves in the radio or microwaves domains, a transmitting antenna, a receiving antenna, a receiver and a processor to determine the properties of the object(s). Radio waves (pulsed or continuous) from the transmitter reflect off the object and return to the receiver, giving the information about the object's location and speed.

A global positioning system (GPS) 732 is a space-based radio-navigation system that provides geo-location and time information to a GPS receiver on any device. The system does not require any data to be transmitted but requires an object to be at least in the line of sight of at least four GPS satellites.

A magnetic compass 734 is an instrument used to determine direction relative to geographic cardinal directions. A magnetic needle of the compass is aligned to the Earth's magnetic field, whereby a torque exerted by the magnetic field on the needle pulls the north point or pole of the needle toward the Earth's north magnetic pole and the opposite end toward the south magnetic pole.

An image capture module 740 is provided for capturing images and image streams of a real environment. More than one camera may be included in the robot 110, including one or more front cameras 742 mounted on the front face of the robot 110, one or more rear-facing cameras 744 mounted on the read face of the robot 110, and one or more side cameras 746 that are mounted on the lateral sides of the robot. Additionally, one or more depth cameras 748 may be included in the robot 110 for capturing depth information of objects in a real environment.

The robot 110 includes speakers 750 for providing audio output. Also, a microphone 752 may be included for capturing audio from the real environment, including sounds from the ambient environment, commands provided by the user, etc. The microphone 752 may be a microphone array that has the capability to focus on sounds from specific direction by filtering out other ambient sounds.

LEDs 754 are provided as visual indicators of statuses of the robot 110. For example, an LED may indicate battery level, power on, etc. IR lights 756 are provided to enable detection of objects when visible light is not available. Motor drive controller 758 is used to control movement of the robot. The motor drive controller 758 is connected to wheels or treads or other mechanism used for moving the robot and includes motor means to move the robot in specific directions, regulate the speed, limit torque, and for overall navigation of the robot in a geo-location. An interface module 760 includes various sub-modules that are used to provide an interface for one or more devices. A USB interface 762 is included as one example of an interface for enabling connection of peripheral devices, or connection to other devices, such as other portable devices, computers, etc. In various implementations of the robot 110, any of various kinds of interfaces may be included to enable greater connectivity of the robot 110. A controller interface is included as an example of an interface for enabling receiving and charging of one or more controllers. A drone interface (referenced herein as "Drone Charge Station") 766 may be included for enabling receiving and charging of a drone device. The drone device may include a camera in its body and can be deployed from the robot to capture an overhead view of the geo-location in which the robot is located. The overhead view may be used to generate a three-dimensional mapping of the space in the geo-location, which can be used to move and position the robot in relation to a user or an object of interest.

A communication module 770 may be used to provide various communication links to different devices within the system. For example, a communications link 772 may be included for connection to other devices. In one embodiment, the communications link 772 utilizes infrared transmission for wireless communication. In other embodiments, the communications link 772 may utilize any of various wireless or wired transmission protocols for communication with other devices. A WiFi module 774 is included for enabling connection to the Internet via wireless networking technologies. An ultra-sonic communications 776 is included to facilitate communication with other devices using ultra-sonic technologies. A Bluetooth module 778 is included for enabling wireless connection to other devices. A projector 780 is included for enabling the robot to project images of content identified for the user on to a display surface identified in the geo-location. The projector 780 may include logic to evaluate the display surface on which the images of content are to be projected to ensure that the display surface is conducive for projection (e.g., is not highly reflective) prior to projecting the images.

Input buttons/sensors 718 are included to provide an input interface for the user. Any of various kinds of input interfaces may be included, such as buttons, touchpad, joystick, trackball, touch screen, keypad, etc.

Bio-sensors 718 are included to enable detection of physiological (i.e., biometric) data from a user. In one implementation, the bio-sensors 718 include one or more dry electrodes for detecting bio-electric signals of the user through the user's skin. In some other implementations, the bio-sensors 718 are configured to detect bio-electric signals generated from remotely located bio-sensors, such as optical bio-sensors, etc., or body attached sensors, such as heart rate monitor or pulse oximeter, etc., disposed on or in the body of the user using wireless communications protocol.

AI logic 114 is included to enable the robot to detect presence of a user from signals received from various sensors, map the space in the geo-location of the robot, position the robot to an area proximate to the user based on the mapped space, monitor the user in the geo-location, capture images of the user performing an activity and provide feedback. The feedback uses machine learning algorithm to detect activity performed by the user, intelligently identify the changes that is to be performed by the user and provide instructions to the user to perform the change. A geo space mapper 115a is included in the AI logic 114 to map the space in the geo-location in either a 2-dimensional or 3-dimensional format. A sensor fusion module 117a is included in the AI logic to merge data obtained from various sensors and to intelligently generate a model of a user based on the data from the various sensors.

The foregoing components of robot 110 have been described as merely exemplary components that may be included in robot 110. In various embodiments of the invention, the robot 110 may or may not include some of the various aforementioned components. Embodiments of the robot 110 may additionally include other components not presently described, but known in the art, for purposes of facilitating aspects of the present invention as herein described.

It will be appreciated by those skilled in the art that in various embodiments of the invention, the aforementioned handheld device may be utilized in conjunction with an interactive application displayed on a display to provide various interactive functions. The exemplary embodiments described herein are provided by way of example only, and not by way of limitation.

Figure 8:
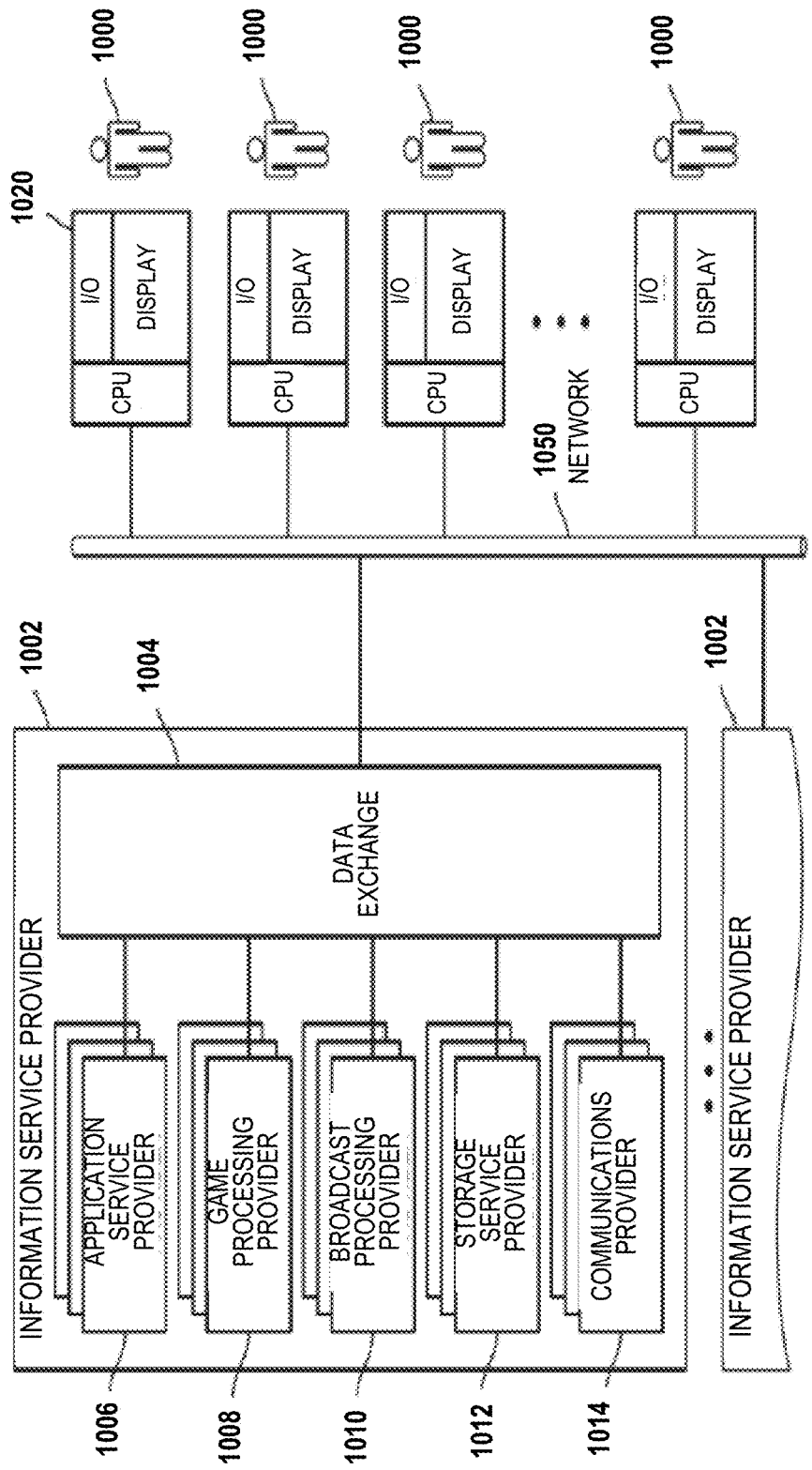
FIG. 8 illustrates an exemplary Information Service Provider architecture for delivering informational content and services to users who are geographically dispersed and connected via network, in accordance with one implementation of the present invention.

FIG. 8 illustrates an implementation of an Information Service Provider architecture that may be used in providing access to different online applications. Information Service Providers (ISP) 1070 deliver a multitude of information services to users 1082 geographically dispersed and connected via network 1086. Although the various implementations have been discussed with reference to providing fast access to online applications, such as games, the implementations can be extended to provide one or more types of other services. For example, an ISP can deliver just one type of service, such as an exercise routine, or a variety of services such as physical fitness routines, games, and other user-preferred content updates. Additionally, the services offered by each ISP may be dynamic, that is, services can be added or taken away at any point in time. Thus, the ISP providing a particular type of service to a particular individual can change over time. For example, a user may be served by an ISP in near proximity to the user while the user is in her home town, and the user may be served by a different ISP when the user travels to a different city. The home-town ISP will transfer the required information and data from the user's gaming or access profile to the new ISP through the connection module, such that the user information "follows" the user to the new city making the data closer to the user and easier to access. In another implementation, a master-server relationship may be established between a master ISP, which manages the information for the user, and a server ISP that interfaces directly with the user under control from the master ISP. In another implementation, the data is transferred from one ISP to another ISP (i.e., during switching of data center assigned to the user) as the client moves around the world and such transfer may be based on a compatibility of services provided by the respective ISPs to make the ISP 1070 in better position to service the user be the one that delivers these services.

ISP 1070 includes Application Service Provider (ASP) 1072, which provides computer-based services to customers over a network. Software offered using an ASP model is also sometimes called on-demand software or software as a service (SaaS). A simple form of providing access to a particular application program (such as customer relationship management) is by using a standard protocol such as HTTP. The application software resides on a vendor's system, for example, and is accessed by users through a web browser using HTML, or by a special purpose client software provided by the vendor, or via other remote interface such as a thin client.

Services delivered over a wide geographical area often use cloud computing. Cloud computing is a style of computing in which dynamically scalable and often virtualized resources are provided as a service over the Internet. Users do not need to be an expert in the technology infrastructure in the "cloud" that supports them. Cloud computing can be divided into different services, such as Infrastructure as a Service (IaaS), Platform as a Service (PaaS), and Software as a Service (SaaS). Cloud computing services often provide common business applications online that are accessed from a web browser, while the software and data are stored on the servers. The term cloud is used as a metaphor for the Internet (e.g., using servers, storage and logic), based on how the Internet is depicted in computer network diagrams and is an abstraction for the complex infrastructure it conceals.

Further, ISP 1070 includes an interactive application server, such as a Game Processing Server (GaPS) 1074 which is used by game clients to play single and multiplayer video games. Most video games played over the Internet operate via a connection to a game server. Typically, games use a dedicated server application that collects data from players and distributes it to other players. This is more efficient and effective than a peer-to-peer arrangement, but it requires a separate server to host the server application. In another implementation, the GaPS establishes communication between the players and their respective game-playing devices exchange information without relying on the centralized GaPS.

Dedicated GaPSs are servers which run independently of the client. Such servers are usually run on dedicated hardware located in data centers, providing more bandwidth and dedicated processing power. Dedicated servers are the preferred method of hosting game servers for most PC-based multiplayer games. Massively multiplayer online games run on dedicated servers usually hosted by the software company that owns the game title, allowing them to control and update content.

Broadcast Processing Server (BPS) 1076 distributes audio or video signals to an audience. Broadcasting to a very narrow range of audience is sometimes called narrowcasting. The final leg of broadcast distribution is how the signal gets to the listener or viewer, and it may come over the air as with a radio station or TV station to an antenna and receiver, or may come through cable TV or cable radio (or "wireless cable") via the station or directly from a network. The Internet may also bring either radio or TV to the recipient, especially with multicasting allowing the signal and bandwidth to be shared. Historically, broadcasts have been delimited by a geographic region, such as national broadcasts or regional broadcast. However, with the proliferation of fast internet, broadcasts are not defined by geographies as the content can reach almost any country in the world.

Storage Service Provider (SSP) 1078 provides computer storage space and related management services. SSPs also offer periodic backup and archiving. By offering storage as a service, users can order more storage as required. Another major advantage is that SSPs include backup services and users will not lose all their data if their computers' hard drives fail. Further, a plurality of SSPs can have total or partial copies of the user data, allowing users to access data in an efficient way independently of where the user is located or the device being used to access the data. For example, a user can access personal files in the home computer, as well as in a mobile phone while the user is on the move.

Communications Provider 1080 provides connectivity to the users. One kind of Communications Provider is an Internet Service Provider (ISP) which offers access to the Internet. The ISP connects its customers using a data transmission technology appropriate for delivering Internet Protocol datagrams, such as dial-up, DSL, cable modem, fiber, wireless or dedicated high-speed interconnects. The Communications Provider can also provide messaging services, such as e-mail, instant messaging, and SMS texting. Another type of Communications Provider is the Network Service provider (NSP) which sells bandwidth or network access by providing direct backbone access to the Internet. Network service providers may consist of telecommunications companies, data carriers, wireless communications providers, Internet service providers, cable television operators offering high-speed Internet access, etc.

Data Exchange 1088 interconnects the several modules inside ISP 1070 and connects these modules to users 1082 via network 1086. Data Exchange 1088 can cover a small area where all the modules of ISP 1070 are in close proximity, or can cover a large geographic area when the different modules are geographically dispersed. For example, Data Exchange 1088 can include a fast Gigabit Ethernet (or faster) within a cabinet of a data center, or an intercontinental virtual area network (VLAN).

Users 1082 access the remote services with client device 1084, which includes at least a CPU, a memory, a display and I/O. The client device can be a PC, a mobile phone, a netbook, tablet, gaming system, a PDA, etc. In one implementation, ISP 1070 recognizes the type of device used by the client and adjusts the communication method employed. In other cases, client devices use a standard communications method, such as HTML, to access ISP 1070.

Embodiments of the present invention may be practiced with various computer system configurations including hand-held devices, microprocessor systems, microprocessor-based or programmable consumer electronics, minicomputers, mainframe computers and the like. The invention can also be practiced in distributed computing environments where tasks are performed by remote processing devices that are linked through a wire-based or wireless network.

With the above embodiments in mind, it should be understood that the invention can employ various computer-implemented operations involving data stored in computer systems. These operations are those requiring physical manipulation of physical quantities. Any of the operations described herein that form part of the invention are useful machine operations. The invention also relates to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

The invention can also be embodied as computer readable code on a computer readable medium. Alternately, the computer readable code may be downloaded from a server using the data exchange interconnects described above. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing invention has been described in some detail for purposes of clarity of understanding, it will be apparent that certain changes and modifications can be practiced within the scope of the appended claims. Accordingly, the present implementations are to be considered as illustrative and not restrictive, and the invention is not to be limited to the details given herein, but may be modified within the scope and equivalents of the described implementations.

An exemplary overall system architecture of a gaming console is described herein. An example gaming console may include a Sony® Playstation 3® (PS3) or a Playstation 4® (PS4) entertainment device, which may be compatible with controllers for implementing an embodiment of the present invention. Although the PS3 gaming console system architecture is explained in detail, it should be noted that the various implementations described herein can be extended to system architecture of a different gaming console or computing device. A system unit is provided, with various peripheral devices connectable to the system unit. The system unit is similar to the cloud gaming system 300 of FIG. 1. The system unit comprises: a processor, which may be a 8 core processor, as in PS3, or a multi-core processor, as in PS4; a Rambus® dynamic random access memory (XDRAM) unit, as in PS3, or a graphics dynamic random access memory, such as a GDDR5, as in PS4; a Reality Synthesizer graphics unit (e.g., 550 MHz GPU) with a dedicated video random access memory (VRAM) unit, as in PS3, or 800 or 900 MHz GPU with shared graphics memory in PS4 and PS4 Pro; and an I/O bridge. The system unit also comprises a Blu Ray® Disk Read Only Memory (BD-ROW)) (optical) disk reader for reading from a disk and a removable slot-in hard disk drive (HDD), accessible through the I/O bridge. Optionally the system unit also comprises a memory card reader for reading compact flash memory cards, Memory Stick® memory cards and the like, which is similarly accessible through the I/O bridge and in PS4, a built-in DVR to record games.

The I/O bridge also connects to six Universal Serial Bus (USB) 2.0 ports; a gigabit Ethernet port; an IEEE 802.11b/g wireless network (Wi-Fi) port; and a Bluetooth® wireless link port capable of supporting of up to seven Bluetooth connections.

In operation the I/O bridge handles all wireless, USB and Ethernet data, including data from one or more game controllers (DualShock 3 controller, as in PS3, or a PS4 DualShock 4 controller, as in PS4, etc.). For example when a user is playing a game, the I/O bridge receives data from the game controller via a Bluetooth link and directs it to the processor (in PS3) or multi-core processor (in PS4), which updates the current state of the game accordingly. Further, other image and move sensors provide data captured during game play of the user, to the I/O bridge, which directs it to the respective processor. The game controllers (e.g., game controllers of PS4) include a share button option for sharing a game, a clickable touchpad, a rechargeable battery (lithium-ion or other type), etc.

The wireless, USB and Ethernet ports also provide connectivity for other peripheral devices in addition to game controllers, such as: a remote control; a keyboard; a mouse; a portable entertainment device such as a Sony Playstation Portable® entertainment device; a video camera such as an EyeToy® video camera; a microphone headset; and a removable hard drive. Such peripheral devices may therefore in principle be connected to the system unit wirelessly; for example the portable entertainment device may communicate via a Wi-Fi ad-hoc connection, whilst the microphone headset may communicate via a Bluetooth link.

The provision of these interfaces means that the Playstation 3 device is also potentially compatible with other peripheral devices such as digital video recorders (DVRs), set-top boxes, digital cameras, portable media players, Voice over IP telephones, mobile telephones, printers and scanners.

In addition, a legacy memory card reader may be connected to the system unit via a USB port, enabling the reading of memory cards of the kind used by the Playstation® or Playstation 2® devices.

In the present implementation, the game controller is operable to communicate wirelessly with the system unit via the Bluetooth link. However, the game controller can instead be connected to a USB port, thereby also providing power by which to charge the battery of the game controller. In addition to one or more analog joysticks and conventional control buttons, the game controller is sensitive to motion in six degrees of freedom, corresponding to translation and rotation in each axis. Consequently gestures and movements by the user of the game controller may be translated as inputs to a game in addition to or instead of conventional button or joystick commands. Optionally, other wirelessly enabled peripheral devices such as the Playstation™ Portable device may be used as a controller. In the case of the Playstation™ Portable device, additional game or control information (for example, control instructions or number of lives) may be provided on the screen of the device. Other alternative or supplementary control devices may also be used, such as a dance mat (not shown), a light gun (not shown), a steering wheel and pedals (not shown) or bespoke controllers, such as a single or several large buttons for a rapid-response quiz game (also not shown).

The remote control is also operable to communicate wirelessly with the system unit via a Bluetooth link. The remote control comprises controls suitable for the operation of the Blu Ray™ Disk BD-ROM reader and for the navigation of disk content.

The Blu Ray™ Disk BD-ROM reader is operable to read Compact Disc, read only memory (CD-ROMs) compatible with the Playstation and PlayStation 2 devices, in addition to conventional pre-recorded and recordable compact discs (CDs), and so-called Super Audio CDs. The Blu Ray™ Disk BD-ROM reader is also operable to read Digital versatile disc-read only memory (DVD-ROMs) compatible with the Playstation2™ and PlayStation 3™ devices, in addition to conventional pre-recorded and recordable DVDs. The Blu Ray™ Disk BD-ROM reader is further operable to read BD-ROMs compatible with the Playstation 3 device, as well as conventional pre-recorded and recordable Blu-Ray Disks.

The system unit is operable to supply audio and video, either generated or decoded by the Playstation 3 or Playstation 4 device via the Reality Synthesizer graphics unit, through audio and video connectors to a display and sound output device such as a monitor or television set having a display and one or more loudspeakers. The audio connectors may include conventional analogue and digital outputs whilst the video connectors may variously include component video, S-video, composite video and one or more High Definition Multimedia Interface (HDMI) outputs. Consequently, video output may be in formats such as PAL or NTSC, or in 720p, 1080i or 1080p high definition and 4K, HDR.

Audio processing (generation, decoding and so on) is performed by the Processor. For example, the Playstation 3 device's operating system supports Dolby® 5.1 surround sound, Dolby® Theatre Surround (DTS), and the decoding of 7.1 surround sound from Blu-Ray® disks.

In the present implementation, the video camera includes a CMOS (Complementary Metal Oxide Semiconductor) image sensor (although a charge-coupled device (CCD) image sensor may also be used), an LED indicator, and hardware-based real-time data compression and encoding apparatus so that compressed video data may be transmitted in an appropriate format such as an intra-image based MPEG (motion picture expert group) standard for decoding by the system unit. The camera LED indicator is arranged to illuminate in response to appropriate control data from the system unit, for example to signify adverse lighting conditions. Implementations of the video camera may variously connect to the system unit via a USB, Bluetooth or Wi-Fi communication port. Implementations of the video camera may include one or more associated microphones and also be capable of transmitting audio data. In implementations of the video camera, the CCD may have a resolution suitable for high-definition video capture. In use, images captured by the video camera may for example be incorporated within a game or interpreted as game control inputs.

In general, in order for successful data communication to occur with a peripheral device such as a video camera or remote control via one of the communication ports of the system unit, an appropriate piece of software such as a device driver should be provided. Device driver technology is well-known and will not be described in detail here, except to say that the skilled man will be aware that a device driver or similar software interface may be required in the present implementation described.

The Processor has an architecture comprising four basic components: external input and output structures comprising a memory controller and a dual bus interface controller; a main processor referred to as the Power Processing Element; eight co-processors referred to as Synergistic Processing Elements (SPEs); and a circular data bus connecting the above components referred to as the Element Interconnect Bus. The total floating point performance of the Processor is 218 GFLOPS, compared with the 6.2 GFLOPs of the Playstation 2 device's Emotion Engine.

The Power Processing Element (PPE) is based upon a two-way simultaneous multithreading Power compliant PowerPC core (PPU) running with an internal clock of 3.2 GHz. It comprises a 512 kB level 2 (L2) cache and a 32 kB level 1 (L1) cache. The PPE is capable of eight single position operations per clock cycle, translating to 25.6 GFLOPs at 3.2 GHz. The primary role of the PPE is to act as a controller for the Synergistic Processing Elements, which handle most of the computational workload. In operation the PPE maintains a job queue, scheduling jobs for the Synergistic Processing Elements and monitoring their progress. Consequently each Synergistic Processing Element runs a kernel whose role is to fetch a job, execute it and synchronized with the PPE.

Each Synergistic Processing Element (SPE) comprises a respective Synergistic Processing Unit (SPU), and a respective Memory Flow Controller (MFC) comprising in turn a respective Dynamic Memory Access Controller (DMAC), a respective Memory Management Unit (MMU) and a bus interface (not shown). Each SPU is a RISC processor clocked at 3.2 GHz and comprising 256 kB local RAM, expandable in principle to 4 GB. Each SPE gives a theoretical 25.6 GFLOPS of single precision performance. An SPU can operate on 4 single precision floating point members, 4 32-bit numbers, 8 16-bit integers, or 16 8-bit integers in a single clock cycle. In the same clock cycle it can also perform a memory operation. The SPU does not directly access the system memory XDRAM 1426; the 64-bit addresses formed by the SPU are passed to the MFC which instructs its DMA controller to access memory via the Element Interconnect Bus and the memory controller.

The Element Interconnect Bus (EIB) is a logically circular communication bus internal to the Processor which connects the above processor elements, namely the PPE, the memory controller, the dual bus interface and the 8 SPEs, totaling 12 participants. Participants can simultaneously read and write to the bus at a rate of 8 bytes per clock cycle. As noted previously, each SPE comprises a DMAC for scheduling longer read or write sequences. The EIB comprises four channels, two each in clockwise and anti-clockwise directions. Consequently for twelve participants, the longest step-wise data-flow between any two participants is six steps in the appropriate direction. The theoretical peak instantaneous EIB bandwidth for 12 slots is therefore 96B per clock, in the event of full utilization through arbitration between participants. This equates to a theoretical peak bandwidth of 307.2 GB/s (gigabytes per second) at a clock rate of 3.2 GHz (giga hertz).

The memory controller comprises an XDRAM interface, developed by Rambus Incorporated. The memory controller interfaces with the Rambus XDRAM 1426 with a theoretical peak bandwidth of 25.6 GB/s.

The dual bus interface comprises a Rambus FlexIO® system interface. The interface is organized into 12 channels each being 8 bits wide, with five paths being inbound and seven outbound. This provides a theoretical peak bandwidth of 62.4 GB/s (36.4 GB/s outbound, 26 GB/s inbound) between the Processor and the I/O Bridge via controller and the Reality Synthesizer graphics unit via controller.

Data sent by the Processor to the Reality Synthesizer graphics unit will typically comprise display lists, being a sequence of commands to draw vertices, apply textures to polygons, specify lighting conditions, and so on.

Embodiments may include capturing depth data to better identify the real-world user and to direct activity of an avatar or scene. The object can be something the person is holding or can also be the person's hand. In this description, the terms "depth camera" and "three-dimensional camera" refer to any camera that is capable of obtaining distance or depth information as well as two-dimensional pixel information. For example, a depth camera can utilize controlled infrared lighting to obtain distance information. Another exemplary depth camera can be a stereo camera pair, which triangulates distance information using two standard cameras. Similarly, the term "depth sensing device" refers to any type of device that is capable of obtaining distance information as well as two-dimensional pixel information.

Recent advances in three-dimensional imagery have opened the door for increased possibilities in real-time interactive computer animation. In particular, new "depth cameras" provide the ability to capture and map the third-dimension in addition to normal two-dimensional video imagery. With the new depth data, embodiments of the present invention allow the placement of computer-generated objects in various positions within a video scene in real-time, including behind other objects.

Moreover, embodiments of the present invention provide real-time interactive gaming experiences for users. For example, users can interact with various computer-generated objects in real-time. Furthermore, video scenes can be altered in real-time to enhance the user's experience. For example, computer generated costumes can be inserted over the user's clothing, and computer generated light sources can be utilized to project virtual shadows within a video scene. Hence, using the embodiments of the present invention and a depth camera, users can experience an interactive environment within their own living room. Similar to normal cameras, a depth camera captures two-dimensional data for a plurality of pixels that comprise the video image. These values are color values for the pixels, generally red, green, and blue (RGB) values for each pixel. In this manner, objects captured by the camera appear as two-dimension objects on a monitor.

Embodiments of the present invention also contemplate distributed image processing configurations. For example, the invention is not limited to the captured image and display image processing taking place in one or even two locations, such as in the CPU or in the CPU and one other element. For example, the input image processing can just as readily take place in an associated CPU, processor or device that can perform processing; essentially all of image processing can be distributed throughout the interconnected system. Thus, the present invention is not limited to any specific image processing hardware circuitry and/or software. The embodiments described herein are also not limited to any specific combination of general hardware circuitry and/or software, nor to any particular source for the instructions executed by processing components.

With the above embodiments in mind, it should be understood that the invention may employ various computer-implemented operations involving data stored in computer systems. These operations include operations requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

The above described invention may be practiced with other computer system configurations including hand-held devices, microprocessor systems, microprocessor-based or programmable consumer electronics, minicomputers, mainframe computers and the like. The invention may also be practiced in distributing computing environments where tasks are performed by remote processing devices that are linked through a communications network.

The invention can also be embodied as computer readable code on a computer readable medium. The computer readable medium is any data storage device that can store data which can be thereafter read by a computer system, including an electromagnetic wave carrier. Examples of the computer readable medium include hard drives, such as solid state drives (SSDs), hard disk drives (HDDs), digital video disc (DVD) drives, Bluray®, etc., network attached storage (NAS), read-only memory, random-access memory, CD-ROMs, CD-Rs, CD-RWs, magnetic tapes, and other optical and non-optical data storage devices. The computer readable medium can also be distributed over a network coupled computer system so that the computer readable code is stored and executed in a distributed fashion.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

The invention claimed is:

1. A method for assisting a user during physical training using a robot, comprising:
   detecting presence of the user in a geo-location where the robot is deployed, the user presence confirmed by matching one or more user attributes of the user captured by the robot with corresponding user attributes stored in a user profile for the user;
   the robot moving automatically to a position proximate to the user for an exercise from an exercise routine, to capture one or more images of a posture of the user when the user is performing the exercise, the exercise routine and the exercise identified by analyzing activity history of the user, the activity history maintaining details of activities including an exercise schedule followed by the user at different times, said posture and the position to capture images of the posture of the exercise that the user is currently performing determined from a virtual model generated for the exercise and the robot moving automatically to an additional position identified for the exercise from the virtual model so as to capture one or more additional images showing changes in the posture that include a range of motion for the exercise, the one or more images of the posture are used to construct a model of the user, the model of the user capturing movement of the user is compared against the virtual model performing the exercise, wherein the robot moving automatically to the position and the additional position includes identifying a path for the robot to move in order to avoid one or more real-world objects detected proximate to the user;
   identifying differences in the posture between the model of the user and the virtual model, the differences are processed by machine learning to identify one or more improvements to the posture of the user; and
   providing feedback to the user, the feedback includes the one or more improvements to the posture for the exercise.

2. The method of claim 1, further including,
   continuing to adjust the position of the robot or orientation of one or more sensors of the robot to enable the robot to capture changes to the posture of the user when the user is performing the exercise identified in the exercise routine, the changes to the posture captured by the robot are used to update the model and the feedback provided to the user.

3. The method of claim 1, wherein the robot moving automatically into the position and additional position further includes,
   mapping the geo-location where the user is performing the exercise routine, the mapping identifying locations of real-world objects disposed therein and an area in which the robot can move to reach the position and the additional position to capture the image of the posture; and
   directing the movement of the robot along the path to the position and the additional position within the area, based on the mapping.

4. The method of claim 3, wherein the mapping is a two dimensional mapping defining the area in which the robot can move, or a three-dimensional mapping defining a volume in which the robot or one or more sensors of the robot can move into position to capture the one or more images of the posture.

5. The method of claim 3, wherein the signal includes a request to the user to re-arrange one or more of the real-world objects in the geo-location to enable the robot or one or more sensors of the robot to follow the path and move into the position and the additional position in the geo-location to capture the one or more images of the posture held by the user when the user is performing the exercise routine.

6. The method of claim 1, wherein the exercise routine performed by the user is further identified using verbal cues received from the user, the verbal cues analyzed and used to retrieve instructions for performing the exercise from the exercise routine, the instructions presented to the user so as to assist the user in performing the exercise from the exercise routine.

7. The method of claim 1, wherein the activity history of the user is identified and retrieved using a user identifier from the user profile of the user.

8. The method of claim 1, wherein providing feedback further includes,
   interpreting the posture of the user captured in the one or more images, as the user is performing the exercise to generate the model, the model defined using a skeletal outline that mimics the posture held by the user; and
   providing tips to the user to correct the posture for the exercise in the exercise routine, when a difference is detected from comparison of the model to the virtual model.

9. The method of claim 8, wherein the tips provided include instructions to adjust the posture of the user for the exercise, the tips being provided in an audio format or an image format or a video format, the tips being generated dynamically using the machine learning and tailored based on the difference detected during comparison of the model with the virtual model.

10. The method of claim 9, wherein the image format or the video format is projected on a rendering surface identified in the geo-location proximal to the user or on a screen available on the robot or on a screen of a head mounted display worn by the user when performing the exercise routine.

11. The method of claim 9, wherein providing tips includes identifying a pre-defined instructional video or a pre-defined instructional audio for the exercise associated with the posture and providing the instructional video or the instructional audio for the user to follow.

12. The method of claim 1, wherein detecting presence of the user in the geo-location includes retrieving the user profile of the user stored locally on the robot and matching the user attributes captured by the robot to corresponding user attributes in the user profile.

13. The method of claim 1, wherein detecting presence of the user in the geo-location includes,
   transmitting the user attributes of the user captured by the robot to a server hosted on a cloud system, the server of the cloud system matching the captured user attributes with user attributes of a plurality of users stored in corresponding user profiles on the server to identify a specific one of the user profiles, the specific user profile identifying the user is used in identifying the exercise routine that the user is scheduled to perform.

14. The method of claim 1, wherein the user attributes are captured using one or more sensors of the robot, the user attributes used to perform biometric verification to identify the user, wherein the user attributes include facial features or fingerprints or hand geometry or voice waves or DNA or signature or gesture or any two or more combinations thereof.

15. The method of claim 14, wherein capturing facial features includes capturing retina and iris patterns, or earlobe geometry, or facial outline, or gaze direction, or any two or more combinations thereof.

16. A method for providing feedback for an exercise routine performed by a user, using a robot, comprising:
   detecting the user performing the exercise routine, wherein the exercise routine includes one or more exercises;
   the robot moving automatically to a position proximate to the user to enable capturing of one or more images of a posture of the user when the user is performing an exercise from the exercise routine, the exercise routine and the exercise identified by analyzing activity history of the user, the activity history maintaining details of an activity schedule including the exercise routine followed by the user at different times, said posture and the position to capture the one or more images of the posture of the exercise currently being performed by the user determined from a virtual model generated for the exercise and the robot moving automatically to an additional position identified for the exercise from the virtual model so as to capture one or more additional images showing changes in the posture that include a range of motion for the exercise, the one or more images of the posture are used to construct a model of the user, the model of the user capturing movement of the user is compared against the virtual model performing the exercise, wherein the robot moving automatically to the position and the additional position includes identifying a path for the robot to move in order to avoid one or more real-world objects detected proximate to the user;
   analyzing the one or more images and the one or more additional images of the user performing the exercise to identify differences between the model of the user and the virtual model, the differences are processed by machine learning to identify one or more improvements to the posture of the user; and
   providing feedback to the user, the feedback includes the one or more improvements to the posture for the exercise from the exercise routine.

17. The method of claim 16, wherein capturing the one or more images by the robot includes adjusting a position or orientation of one or more sensors of the robot, wherein the one or more sensors are used to capture the images of the posture and changes in the posture of the user while the user is performing the exercise.

18. The method of claim 16, wherein detecting the user performing the exercise routine further includes,
   capturing movement of the user in a geo-location in which the robot is deployed and
   correlating the movement of the user captured by the robot to the exercise from the exercise routine identified from the activity schedule.

19. The method of claim 16, further including,
   continuing to monitor the posture of the user as the user performs the exercise routine, to determine any change in the posture of the user; and
   when a change in the posture is detected, dynamically adjusting position of the robot to capture one or more images of the change in the posture of the user, the one or more images related to the change in the posture are analyzed to update the model and to provide additional feedback to the user, the additional feedback provided to enable the user to improve the posture for the exercise.

20. The method of claim 19, wherein the change in the posture correlates to the user performing a different exercise within the exercise routine or the user correcting the posture, in response to the feedback received, when performing the exercise from the exercise routine.

21. A method for providing feedback for an exercise routine performed by a user using a robot, comprising:
   receiving instructions from the user, the instructions identifying a specific portion of a body the user would like to target when exercising;
   identifying the exercise routine that targets the specific portion of the body provided in the instructions, the exercise routine identifying different exercises that are to be performed by the user to target the specific portion of the body,
   wherein the exercise routine is identified by analyzing activity history of the user, the activity history maintaining details of activities including an exercise schedule followed by the user at different times and type of exercise routine that the user has performed previously for targeting the specific portion of the body; and
   providing details of an exercise from the exercise routine for the user to follow;
   the robot automatically moving to a position proximate to the user after detecting the user performing the exercise from the exercise routine, the movement enabling the robot to capture images of a posture of the user when performing the exercise, the position identified to capture the posture of the exercise that the user is currently performing and the robot moving automatically to an additional position to capture one or more additional images showing changes in the posture that include a range of motion for the exercise, the posture, the position and the additional position determined from a virtual model generated for the exercise, the one or more images of the posture and the one or more additional images capturing changes to the posture are used to construct a model of the user, the model of the user capturing movement of the user is compared against a virtual model performing the exercise, wherein the robot moving automatically to the position and the additional position includes adjusting a path for moving the robot to avoid one or more detected real-world objects proximate to the user;
   identifying differences between the model of the user and the virtual model, the differences are processed by machine learning to identify one or more improvements to the posture of the user;
   providing feedback to the user, the feedback includes the one or more improvements to the posture of the user for the exercise;
   continuing to monitor the posture of the user as the user continues to perform the exercise routine, the monitoring performed by adjusting the position or the additional position of the robot to capture images of changes in the posture that include the range of motion; and
   updating the model and providing additional feedback to the user based on the changes detected in the posture of the user, the additional feedback provided to enable the user to improve the posture for the exercise in the exercise routine.

22. The method of claim 21, wherein activity history of the user is identified using a user identifier obtained from a user profile of the user.

23. The method of claim 21, wherein identifying the exercise routine further includes, querying activity history of a plurality of users to identify certain ones of the plurality of users following the exercise routine identified for the user and targeting the specific portion of the body, wherein the feedback and the additional feedback are provided based on feedback provided to the certain ones of the plurality of users following the identified exercise routine.

24. The method of claim 21, wherein providing feedback further includes, keeping track of details of each exercise within the exercise routine performed by the user and providing a status for each exercise in the exercise routine, to the user.

25. The method of claim 21, wherein changes in the posture may be a result of a change in the exercise performed by the user during the exercise routine.

* * * * *